(12) United States Patent
Vukicevic et al.

(10) Patent No.: US 7,850,964 B2
(45) Date of Patent: Dec. 14, 2010

(54) BMP-1 PROCOLLAGEN C-PROTEINASE FOR DIAGNOSIS AND TREATMENT OF BONE AND SOFT TISSUE DEFECTS AND DISORDERS

(75) Inventors: Slobodan Vukicevic, Zagreb (HR); Lovorka Grgurevic, Zagreb (HR); Boris Macek, Zagreb (HR)

(73) Assignee: Genera Istrazivanja d.o.o., Kalinovica (HR)

(*) Notice: Subject to any disclaimer, the term of this patent is extended or adjusted under 35 U.S.C. 154(b) by 0 days.

(21) Appl. No.: 12/309,510

(22) PCT Filed: Jul. 23, 2007

(86) PCT No.: PCT/US2007/016605

§ 371 (c)(1),
(2), (4) Date: Jan. 21, 2009

(87) PCT Pub. No.: WO2008/011193

PCT Pub. Date: Jan. 24, 2008

(65) Prior Publication Data

US 2009/0191255 A1 Jul. 30, 2009

Related U.S. Application Data

(60) Provisional application No. 60/832,325, filed on Jul. 21, 2006.

(51) Int. Cl.
*A61K 39/00* (2006.01)
*A61K 39/395* (2006.01)

(52) U.S. Cl. .................................. 424/130.1; 424/139.1
(58) Field of Classification Search ....................... None
See application file for complete search history.

(56) References Cited

U.S. PATENT DOCUMENTS

| | | | |
|---|---|---|---|
| 4,968,590 | A | 11/1990 | Kuberasampath et al. |
| 5,011,691 | A | 4/1991 | Oppermann et al. |
| 5,496,552 | A | 3/1996 | Kuberasampath et al. |
| 5,674,844 | A | 10/1997 | Kuberasampath et al. |
| 6,333,312 | B1 | 12/2001 | Kuberasampath et al. |
| 2003/0215836 | A1 | 11/2003 | Young et al. |
| 2003/0224501 | A1 | 12/2003 | Young et al. |
| 2005/0147602 | A1 | 7/2005 | Lindner |

OTHER PUBLICATIONS

Applicant's Response to the Written Opinion as filed for international application No. PCT/US2007/016605 on Dec. 19, 2008.
International Search Report for international application No. PCT/US2007/016605(Sep. 19, 2008).
Written Opinion of the International Searching Authority for international application No. PCT/US2007/016605 (Sep. 19, 2008).

(Continued)

*Primary Examiner*—Elizabeth C. Kemmerer
(74) *Attorney, Agent, or Firm*—Thomas R. Berka; Leon R. Yankwich; Yankwich & Associates, P.C.

(57) ABSTRACT

Uses of BMP-1 isoforms for diagnosing and treating defects and disorders of bone and soft tissues are described. Also described is a newly isolated variant of the BMP-1 isoform BMP-1-3.

2 Claims, 8 Drawing Sheets

OTHER PUBLICATIONS

Bonnarens et al., Production of a Standard Closed Fracture in Laboratory Animal Bone, *J. Orthop. Res.*, 2: 97-101 (1984).

Borovecki et al., "The role of bone morphogenetic proteins in kidney development and repair" In *Bone Morphogenetic Proteins From Laboratory to Clinical Practice*, (Vukicevic and Sampth, eds.) (Birkhäuser Verlag, Basel, 2002), pp. 263-288.

Ge et al., GDF11 Forms a Bone Morphogenetic Protein 1-Activated Latent Complex That Can Modulate Nerve Growth Factor-Induced Differentiation of PC12 Cells, *Mol. Cell. Biol.*, 25(14): 5846-5858 (2005).

Griffith et al., Three-dimensional structure of recombinant human osteogenic protein 1: Structural paradigm for the transforming growth factor β superfamily, *Proc. Natl. Acad. Sci. USA*, 93: 878-883 (1996).

Greenspan, Biosynthetic Processing of Collagen Molecules, *Top. Curr. Chem.*, 247: 149-183 (2005).

Greenspan et al., Developmental Roles of the BMP1/TLD Metalloproteinases, *Birth Defect Res.(Part C)*, 78: 47-68 (2006).

Grgurevic et al., Urine release of systemically administered bone morphogenetic protein hybrid molecule, *J. Nephrol.*, 20: 311-319 (2007).

Hildebrand et al., Quantification of Bone Microarchitecture with the Structure Model Index, *Comp. Meth. Biochem. Eng.*, 1: 15-23 (1997).

Hillman et al., An unappreciated role of RNA surveillance, *Genome Biol.*, 5(R8): 1-16 (2004).

Hoffmann et al., Perspectives in the biological function, the technical and therapeutic application of bone morphogenetic proteins, *Appl. Microbiol. Biotechnol.*, 57: 294-308 (2001).

Holliger et al., "Diabodies": Small bivalent and bispecific antibody fragments *Proc. Natl. Acad. Sci. USA*, 90: 6444-6448 (1993).

Iozzo, Basement Membrane Proteoglycans: From Cellar to Ceiling, *Nat. Rev. Mol. Cell. Biol.*, 6: 646-656 (2005).

Janitz et al., Three alternatively spliced variants of the gene coding for the human bone morphogenetic protein-1, *J. Mol. Med.*, 76: 141-146 (1998).

Kessler et al., Bone Morphogenetic Protein-1: The Type I Procollagen C-Proteinase, *Science*, 271: 360-362 (1996).

Leighton et al., Paired Basic/Furin-like Proprotein Convertase Cleavage of Pro-BMP-1 in the *trans*-Golgi Network, *J. Biol. Chem.*, 278(20): 18478-18484 (2003).

Li et al., The C-proteinase that processes procollagens to fibrillar collagens is identical to the protein previously identified as bone morphogenic protein-1, *Proc. Natl. Acad. Sci.*, 93: 5127- 5130 (1996).

Marques et al., Production of a DDP Activity Gradient in the Early Drosophila Embryo through the Opposing Actions of the SOG and TLD Proteins, *Cell*, 91: 417-426 (1997).

Martinovic et al., Requirement of a bone morphogenetic protein for the maintenance and stimulation of osteoblast differentiation, *Arch. Cytol. Histol.*, 1: 23-36 (2006).

Oslen et al., Improved peptide identification in proteomics by two consecutive stages of mass spectrometric fragmentation, *Proc. Natl. Acad. Sci. USA*, 101(37): 13417-13422 (2004).

Paralkar et al., An EP2 receptor-selective prostaglandin $E^2$ agonist induces bone healing, *Proc. Natl. Acad. Sci. USA*, 100(11): 6736-6740 (2003).

Reddi, BMP-1: Resurrection As Procollagen C-Proteinase, *Science*, 271: 463 (1996).

Reddi, J., Bone Morphogenetic Proteins: From Basic Science to Clinical Applications, *J. Bone Joint Surg.*, 83-A (Supp.1): S-1—S-6 (2001).

Sampath et al., Dissociative extraction and reconstitution of extracellular matrix components involved in local bone differentiation, *Proc. Natl. Acad. Sci. USA*, 78(12): 7599-7603 (1981).

Sampath et al., Homology of bone-inductive proteins from human, monkey, bovine, and rat extracellular matrix, *Proc. Natl. Acad. Sci. USA*, 80: 6591-6595 (1983).

Sampath et al., Isolation of osteogenin, an extracellular matrix-associated, bone-inductive protein, by heparin affinity chromatography, *Proc. Natl. Acad. Sci. USA*, 84: 7109-7113 (1987).

Sieron et al., Structure and Function of Procollagen C-Proteinase (mTolloid) Domains Determined by Protease Digestion, Circular Dichroism, Binding to Procollagen Type I, and Computer Modeling, *Biochem.*, 39: 3231-3239 (2000).

Simic et al., Systemically Administered Bone Morphogenetic Protein-6 Restores Bone in Aged Ovariectomized Rats by Increasing Bone Formation and Suppressing Bone Resorption, *J. Biol. Chem.*, 281(35): 25509-25521 (2006).

Takahara et al., Bone Morphogenetic Protein-1 and a Mammalian Tolloid Homologue (mTld) Are Encoded by Alternatively Spliced Transcripts Which Are Differentially Expressed in Some Tissues, *J. Biol. Chem.*, 269(51): 32572-32578 (1994).

Urist et al.,Human Bone Morphogenetic Protein (hBMP)[1] (41630), *Proc. Soc. Exp. Biol. Med.*, 173: 194-199 (1983).

Vukicevic et al., Osteogenic Protein-1 (Bone Morphogenetic Protein-7) Reduces Severity of Injury After Ischemic Acute Renal Failure in Rat, *J. Clin. Invest.*, 102(1): 202-214 (1998).

Vukicevic et al., Stimulation of the expression of osteogenic and chondrogenic phenotypes in vitro by osteogenin, *Proc. Natl. Acad. Sci. USA*, 86: 8793-8797 (1989).

Wolfman et al., Activation of latent myostatin by the BMP-1/tolloid family of metalloproteinases, *Proc. Natl. Acad. Sci. USA*, 100(26): 15842-15846 (2003).

Wozney et al., Novel Regulators of Bone Formation: Molecular Clones and Activities, *Science*, 242: 1528-1534 (1988).

International Preliminary Report on Patentability (Chapter II), issued Jan. 20, 2010, in international application No. PCT/US2007/016605 (including Annex).

Extended European Search Report dated Mar. 10, 2010, issued in corresponding European application No. 07836198.7.

Chow et al., "Animal Remnant Kidney Model of Chronic Renal Failure Revisited," Hong Kong J. Nephrology, 5(2): 57-64 (2003).

Klahr, S., "The bone morphogenetic proteins (BMPs). Their role in renal fibrosis and renal function," J. Nephrology, 16(2): 179-185 (2003).

Li, Tingting, et al., "Bone morphogenetic protein 7: a novel treatment for chronic renal and bone disease," Curr. Opin. Nephrol. Hypertens., 13(4): 417-422 (2004).

Scott et al., "Mammalian BMP-1/Tolloid-related metalloproteinases, including novel family member mammalian Tolloid-like 2, have differential enzymatic activities and distributions of expression relevant to patterning and skeletogenesis," Develop. Biol., 213(2): 283-300 (1999).

Turtle et al., "Inhibition of procollagen C-proteinase: Fibrosis and beyond," Expert Opin. Ther. Patents, 14(8): 1185-1197 (2004) .

Klahr et al., "New approaches to delay the progression of chronic renal failure," Kidney Int. Suppl., vol. 61, Supplement 80, pp. S23-S26 (2002).

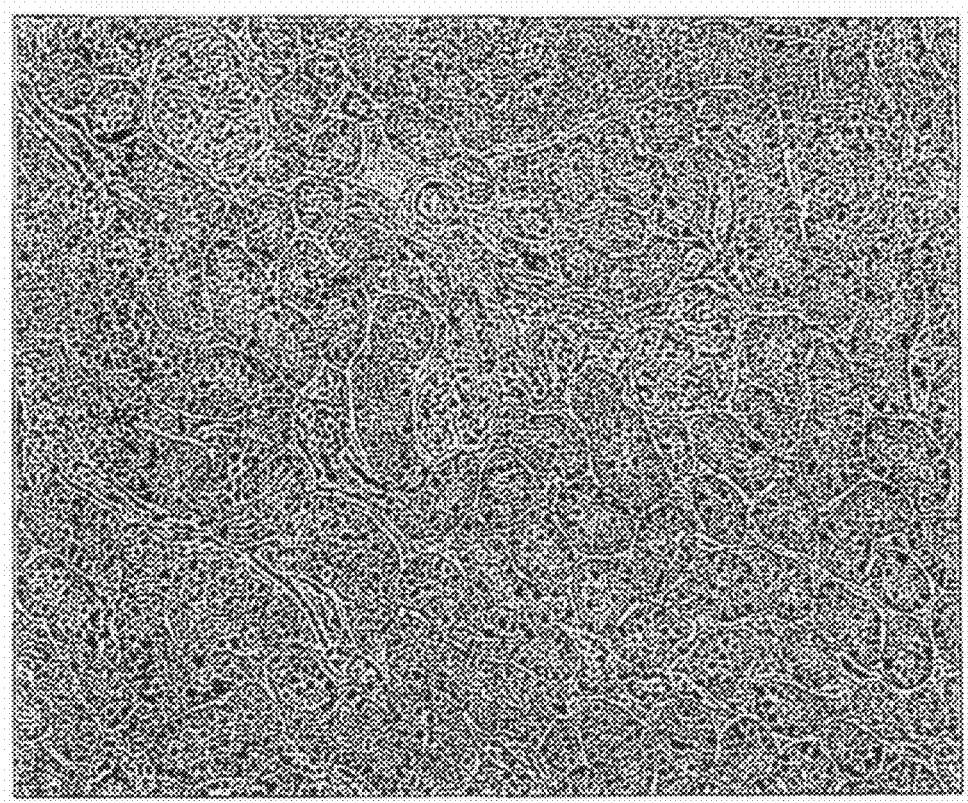
Fig. 2B anti-BMP1-1 and anti-BMP1-3
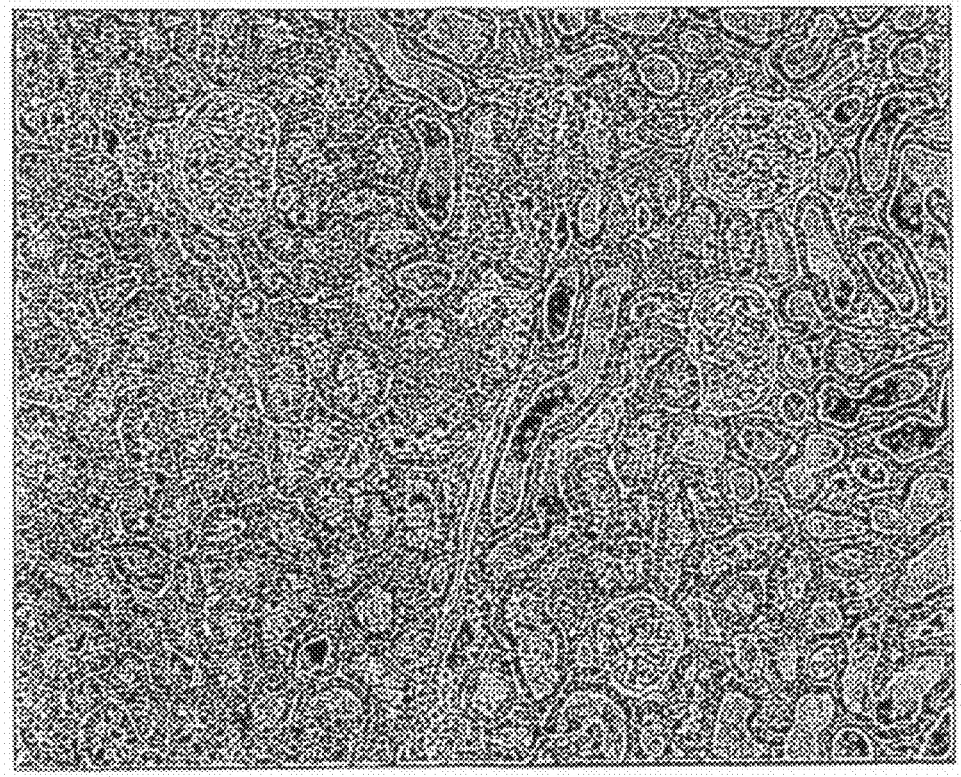
Fig. 2A untreated

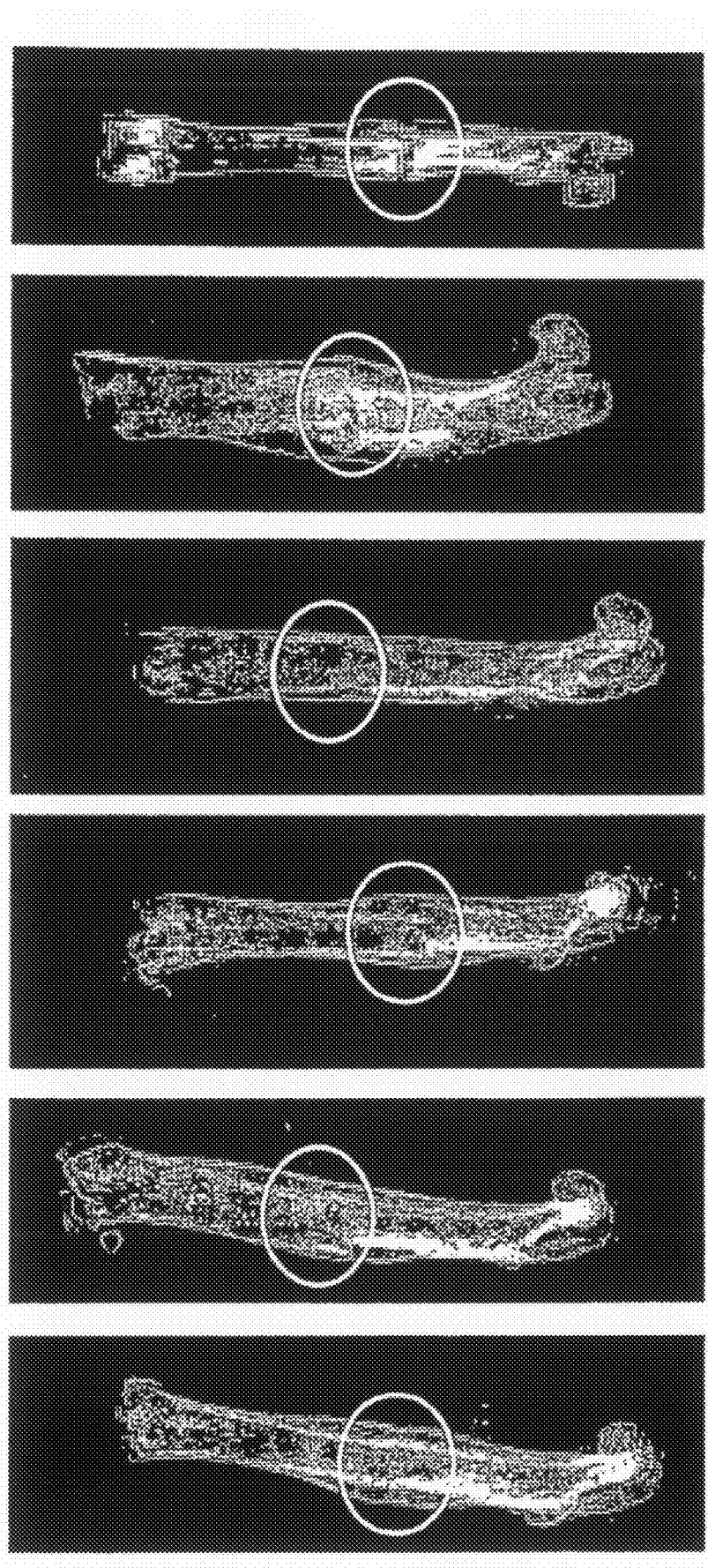

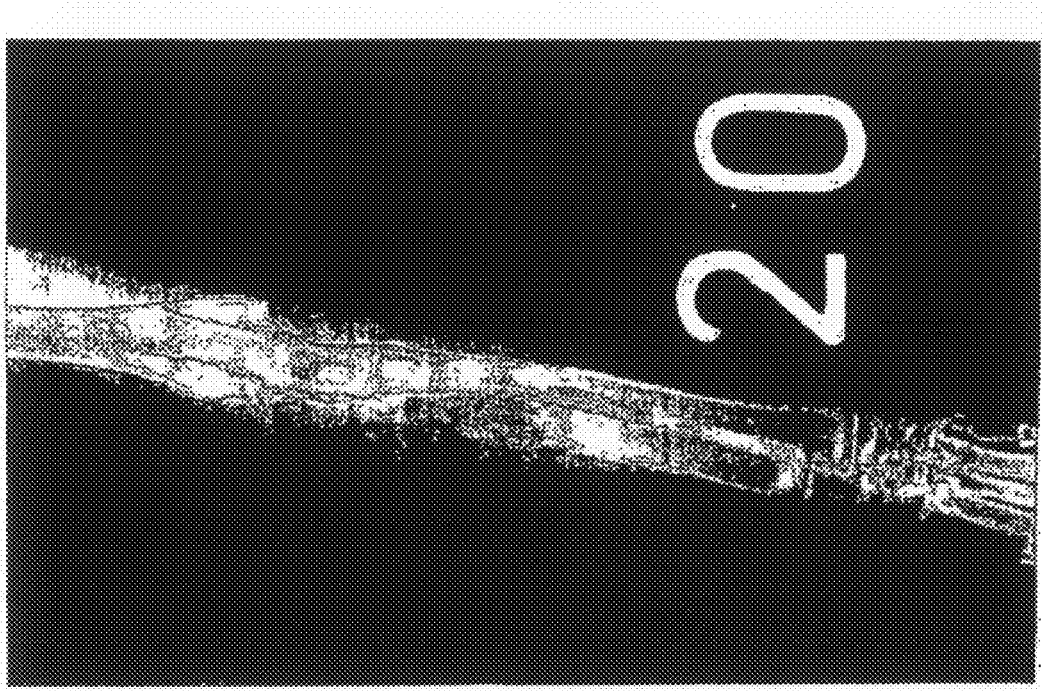
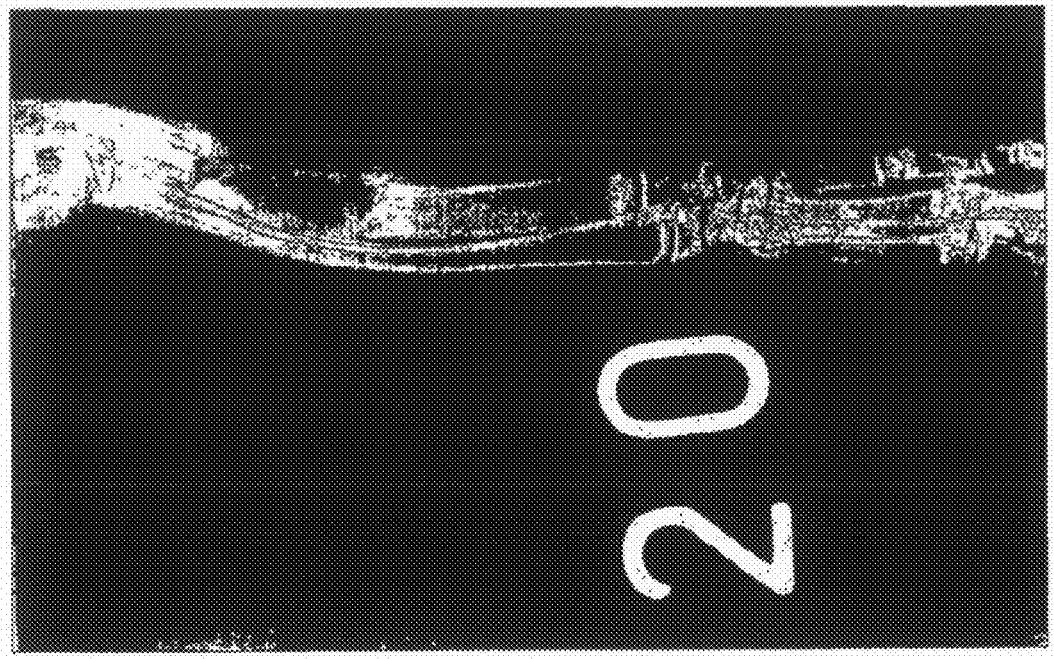
Fig. 7A
Fig. 7B

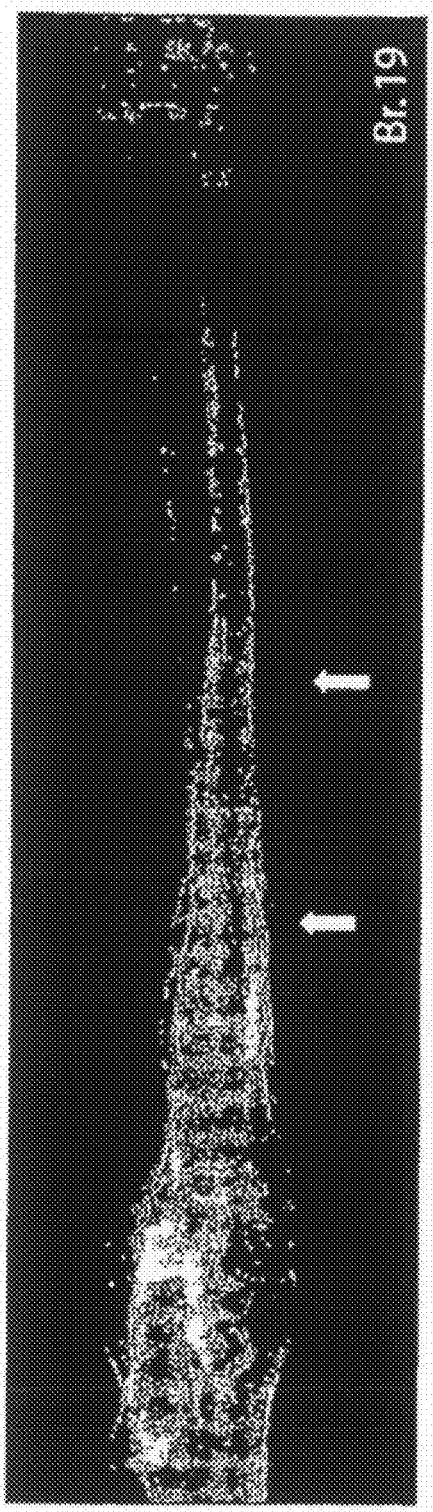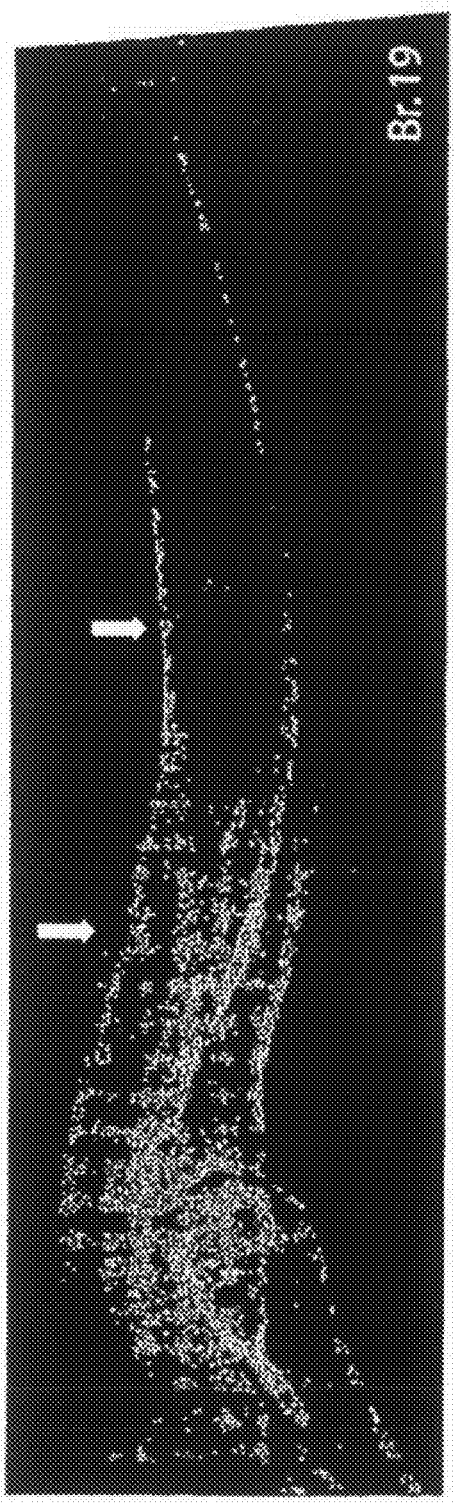

SEQUENCE LISTING

<160> NUMBER OF SEQ ID NOS: 7

<210> SEQ ID NO 1
<211> LENGTH: 730
<212> TYPE: PRT
<213> ORGANISM: Homo sapiens

<400> SEQUENCE: 1

```
Met Pro Gly Val Ala Arg Leu Pro Leu Leu Leu Gly Leu Leu Leu Leu
1               5                   10                  15

Pro Arg Pro Gly Arg Pro Leu Asp Leu Ala Asp Tyr Thr Tyr Asp Leu
            20                  25                  30

Ala Glu Glu Asp Asp Ser Glu Pro Leu Asn Tyr Lys Asp Pro Cys Lys
        35                  40                  45

Ala Ala Ala Phe Leu Gly Asp Ile Ala Leu Asp Glu Glu Asp Leu Arg
    50                  55                  60

Ala Phe Gln Val Gln Gln Ala Val Asp Leu Arg Arg His Thr Ala Arg
65                  70                  75                  80

Lys Ser Ser Ile Lys Ala Ala Val Pro Gly Asn Thr Ser Thr Pro Ser
                85                  90                  95

Cys Gln Ser Thr Asn Gly Gln Pro Gln Arg Gly Ala Cys Gly Arg Trp
            100                 105                 110

Arg Gly Arg Ser Arg Ser Arg Arg Ala Ala Thr Ser Arg Pro Glu Arg
        115                 120                 125

Val Trp Pro Asp Gly Val Ile Pro Phe Val Ile Gly Gly Asn Phe Thr
    130                 135                 140

Gly Ser Gln Arg Ala Val Phe Arg Gln Ala Met Arg His Trp Glu Lys
145                 150                 155                 160

His Thr Cys Val Thr Phe Leu Glu Arg Thr Asp Glu Asp Ser Tyr Ile
                165                 170                 175

Val Phe Thr Tyr Arg Pro Cys Gly Cys Cys Ser Tyr Val Gly Arg Arg
            180                 185                 190

Gly Gly Gly Pro Gln Ala Ile Ser Ile Gly Lys Asn Cys Asp Lys Phe
        195                 200                 205

Gly Ile Val Val His Glu Leu Gly His Val Val Gly Phe Trp His Glu
    210                 215                 220

His Thr Arg Pro Asp Arg Asp Arg His Val Ser Ile Val Arg Glu Asn
```

```
            225                 230                 235                 240
Ile Gln Pro Gly Gln Glu Tyr Asn Phe Leu Lys Met Glu Pro Gln Glu
                245                 250                 255
Val Glu Ser Leu Gly Glu Thr Tyr Asp Phe Asp Ser Ile Met His Tyr
            260                 265                 270
Ala Arg Asn Thr Phe Ser Arg Gly Ile Phe Leu Asp Thr Ile Val Pro
            275                 280                 285
Lys Tyr Glu Val Asn Gly Val Lys Pro Pro Ile Gly Gln Arg Thr Arg
            290                 295                 300
Leu Ser Lys Gly Asp Ile Ala Gln Ala Arg Lys Leu Tyr Lys Cys Pro
305                 310                 315                 320
Ala Cys Gly Glu Thr Leu Gln Asp Ser Thr Gly Asn Phe Ser Ser Pro
                325                 330                 335
Glu Tyr Pro Asn Gly Tyr Ser Ala His Met His Cys Val Trp Arg Ile
            340                 345                 350
Ser Val Thr Pro Gly Glu Lys Ile Ile Leu Asn Phe Thr Ser Leu Asp
            355                 360                 365
Leu Tyr Arg Ser Arg Leu Cys Trp Tyr Asp Tyr Val Glu Val Arg Asp
            370                 375                 380
Gly Phe Trp Arg Lys Ala Pro Leu Arg Gly Arg Phe Cys Gly Ser Lys
385                 390                 395                 400
Leu Pro Glu Pro Ile Val Ser Thr Asp Ser Arg Leu Trp Val Glu Phe
                405                 410                 415
Arg Ser Ser Ser Asn Trp Val Gly Lys Gly Phe Phe Ala Val Tyr Glu
                420                 425                 430
Ala Ile Cys Gly Gly Asp Val Lys Lys Asp Tyr Gly His Ile Gln Ser
            435                 440                 445
Pro Asn Tyr Pro Asp Asp Tyr Arg Pro Ser Lys Val Cys Ile Trp Arg
            450                 455                 460
Ile Gln Val Ser Glu Gly Phe His Val Gly Leu Thr Phe Gln Ser Phe
465                 470                 475                 480
Glu Ile Glu Arg His Asp Ser Cys Ala Tyr Asp Tyr Leu Glu Val Arg
                485                 490                 495
Asp Gly His Ser Glu Ser Ser Thr Leu Ile Gly Arg Tyr Cys Gly Tyr
            500                 505                 510
Glu Lys Pro Asp Asp Ile Lys Ser Thr Ser Ser Arg Leu Trp Leu Lys
            515                 520                 525
Phe Val Ser Asp Gly Ser Ile Asn Lys Ala Gly Phe Ala Val Asn Phe
            530                 535                 540
Phe Lys Glu Val Asp Glu Cys Ser Arg Pro Asn Arg Gly Gly Cys Glu
545                 550                 555                 560
Gln Arg Cys Leu Asn Thr Leu Gly Ser Tyr Lys Cys Ser Cys Asp Pro
                565                 570                 575
Gly Tyr Glu Leu Ala Pro Asp Lys Arg Arg Cys Glu Ala Ala Cys Gly
            580                 585                 590
Gly Phe Leu Thr Lys Leu Asn Gly Ser Ile Thr Ser Pro Gly Trp Pro
            595                 600                 605
Lys Glu Tyr Pro Pro Asn Lys Asn Cys Ile Trp Gln Leu Val Ala Pro
            610                 615                 620
Thr Gln Tyr Arg Ile Ser Leu Gln Phe Asp Phe Phe Glu Thr Glu Gly
625                 630                 635                 640
Asn Asp Val Cys Lys Tyr Asp Phe Val Glu Val Arg Ser Gly Leu Thr
                645                 650                 655
```

```
Ala Asp Ser Lys Leu His Gly Lys Phe Cys Gly Ser Glu Lys Pro Glu
            660                 665                 670

Val Ile Thr Ser Gln Tyr Asn Asn Met Arg Val Glu Phe Lys Ser Asp
            675                 680                 685

Asn Thr Val Ser Lys Lys Gly Phe Lys Ala His Phe Phe Ser Glu Lys
            690                 695                 700

Arg Pro Ala Leu Gln Pro Pro Arg Gly Arg Pro His Gln Leu Lys Phe
705                 710                 715                 720

Arg Val Gln Lys Arg Asn Arg Thr Pro Gln
                725                 730

<210> SEQ ID NO 2
<211> LENGTH: 986
<212> TYPE: PRT
<213> ORGANISM: Homo sapiens

<400> SEQUENCE: 2

Met Pro Gly Val Ala Arg Leu Pro Leu Leu Gly Leu Leu Leu Leu Leu
1               5                   10                  15

Pro Arg Pro Gly Arg Pro Leu Asp Leu Ala Asp Tyr Thr Tyr Asp Leu
                20                  25                  30

Ala Glu Glu Asp Asp Ser Glu Pro Leu Asn Tyr Lys Asp Pro Cys Lys
            35                  40                  45

Ala Ala Ala Phe Leu Gly Asp Ile Ala Leu Asp Glu Glu Asp Leu Arg
        50                  55                  60

Ala Phe Gln Val Gln Gln Ala Val Asp Leu Arg Arg His Thr Ala Arg
65                  70                  75                  80

Lys Ser Ser Ile Lys Ala Ala Val Pro Gly Asn Thr Ser Thr Pro Ser
                85                  90                  95

Cys Gln Ser Thr Asn Gly Gln Pro Gln Arg Gly Ala Cys Gly Arg Trp
            100                 105                 110

Arg Gly Arg Ser Arg Ser Arg Ala Ala Thr Ser Arg Pro Glu Arg
        115                 120                 125

Val Trp Pro Asp Gly Val Ile Pro Phe Val Ile Gly Gly Asn Phe Thr
        130                 135                 140

Gly Ser Gln Arg Ala Val Phe Arg Gln Ala Met Arg His Trp Glu Lys
145                 150                 155                 160

His Thr Cys Val Thr Phe Leu Glu Arg Thr Asp Glu Asp Ser Tyr Ile
                165                 170                 175

Val Phe Thr Tyr Arg Pro Cys Gly Cys Cys Ser Tyr Val Gly Arg Arg
            180                 185                 190

Gly Gly Gly Pro Gln Ala Ile Ser Ile Gly Lys Asn Cys Asp Lys Phe
        195                 200                 205

Gly Ile Val Val His Glu Leu Gly His Val Val Gly Phe Trp His Glu
    210                 215                 220

His Thr Arg Pro Asp Arg Asp Arg His Val Ser Ile Val Arg Glu Asn
225                 230                 235                 240

Ile Gln Pro Gly Gln Glu Tyr Asn Phe Leu Lys Met Glu Pro Gln Glu
                245                 250                 255

Val Glu Ser Leu Gly Glu Thr Tyr Asp Phe Asp Ser Ile Met His Tyr
            260                 265                 270

Ala Arg Asn Thr Phe Ser Arg Gly Ile Phe Leu Asp Thr Ile Val Pro
        275                 280                 285

Lys Tyr Glu Val Asn Gly Val Lys Pro Pro Ile Gly Gln Arg Thr Arg
```

-continued

```
            290                 295                 300
Leu Ser Lys Gly Asp Ile Ala Gln Ala Arg Lys Leu Tyr Lys Cys Pro
305                 310                 315                 320

Ala Cys Gly Glu Thr Leu Gln Asp Ser Thr Gly Asn Phe Ser Ser Pro
                325                 330                 335

Glu Tyr Pro Asn Gly Tyr Ser Ala His Met His Cys Val Trp Arg Ile
                340                 345                 350

Ser Val Thr Pro Gly Glu Lys Ile Ile Leu Asn Phe Thr Ser Leu Asp
                355                 360                 365

Leu Tyr Arg Ser Arg Leu Cys Trp Tyr Asp Tyr Val Glu Val Arg Asp
370                 375                 380

Gly Phe Trp Arg Lys Ala Pro Leu Arg Gly Arg Phe Cys Gly Ser Lys
385                 390                 395                 400

Leu Pro Glu Pro Ile Val Ser Thr Asp Ser Arg Leu Trp Val Glu Phe
                405                 410                 415

Arg Ser Ser Ser Asn Trp Val Gly Lys Gly Phe Phe Ala Val Tyr Glu
                420                 425                 430

Ala Ile Cys Gly Gly Asp Val Lys Lys Asp Tyr Gly His Ile Gln Ser
            435                 440                 445

Pro Asn Tyr Pro Asp Asp Tyr Arg Pro Ser Lys Val Cys Ile Trp Arg
            450                 455                 460

Ile Gln Val Ser Glu Gly Phe His Val Gly Leu Thr Phe Gln Ser Phe
465                 470                 475                 480

Glu Ile Glu Arg His Asp Ser Cys Ala Tyr Asp Tyr Leu Glu Val Arg
                485                 490                 495

Asp Gly His Ser Glu Ser Ser Thr Leu Ile Gly Arg Tyr Cys Gly Tyr
                500                 505                 510

Glu Lys Pro Asp Asp Ile Lys Ser Thr Ser Ser Arg Leu Trp Leu Lys
            515                 520                 525

Phe Val Ser Asp Gly Ser Ile Asn Lys Ala Gly Phe Ala Val Asn Phe
            530                 535                 540

Phe Lys Glu Val Asp Glu Cys Ser Arg Pro Asn Arg Gly Gly Cys Glu
545                 550                 555                 560

Gln Arg Cys Leu Asn Thr Leu Gly Ser Tyr Lys Cys Ser Cys Asp Pro
                565                 570                 575

Gly Tyr Glu Leu Ala Pro Asp Lys Arg Arg Cys Glu Ala Ala Cys Gly
                580                 585                 590

Gly Phe Leu Thr Lys Leu Asn Gly Ser Ile Thr Ser Pro Gly Trp Pro
                595                 600                 605

Lys Glu Tyr Pro Pro Asn Lys Asn Cys Ile Trp Gln Leu Val Ala Pro
610                 615                 620

Thr Gln Tyr Arg Ile Ser Leu Gln Phe Asp Phe Phe Glu Thr Glu Gly
625                 630                 635                 640

Asn Asp Val Cys Lys Tyr Asp Phe Val Glu Val Arg Ser Gly Leu Thr
                645                 650                 655

Ala Asp Ser Lys Leu His Gly Lys Phe Cys Gly Ser Glu Lys Pro Glu
                660                 665                 670

Val Ile Thr Ser Gln Tyr Asn Asn Met Arg Val Glu Phe Lys Ser Asp
                675                 680                 685

Asn Thr Val Ser Lys Lys Gly Phe Lys Ala His Phe Phe Ser Asp Lys
            690                 695                 700

Asp Glu Cys Ser Lys Asp Asn Gly Gly Cys Gln Gln Asp Cys Val Asn
705                 710                 715                 720
```

```
Thr Phe Gly Ser Tyr Glu Cys Gln Cys Arg Ser Gly Phe Val Leu His
                725                 730                 735
Asp Asn Lys His Asp Cys Lys Glu Ala Gly Cys Asp His Lys Val Thr
            740                 745                 750
Ser Thr Ser Gly Thr Ile Thr Ser Pro Asn Trp Pro Asp Lys Tyr Pro
        755                 760                 765
Ser Lys Lys Glu Cys Thr Trp Ala Ile Ser Ser Thr Pro Gly His Arg
    770                 775                 780
Val Lys Leu Thr Phe Met Glu Met Asp Ile Glu Ser Gln Pro Glu Cys
785                 790                 795                 800
Ala Tyr Asp His Leu Glu Val Phe Asp Gly Arg Asp Ala Lys Ala Pro
                805                 810                 815
Val Leu Gly Arg Phe Cys Gly Ser Lys Lys Pro Glu Pro Val Leu Ala
            820                 825                 830
Thr Gly Ser Arg Met Phe Leu Arg Phe Tyr Ser Asp Asn Ser Val Gln
        835                 840                 845
Arg Lys Gly Phe Gln Ala Ser His Ala Thr Glu Cys Gly Gly Gln Val
    850                 855                 860
Arg Ala Asp Val Lys Thr Lys Asp Leu Tyr Ser His Ala Gln Phe Gly
865                 870                 875                 880
Asp Asn Asn Tyr Pro Gly Gly Val Asp Cys Glu Trp Val Ile Val Ala
                885                 890                 895
Glu Glu Gly Tyr Gly Val Glu Leu Val Phe Gln Thr Phe Glu Val Glu
            900                 905                 910
Glu Glu Thr Asp Cys Gly Tyr Asp Tyr Met Glu Leu Phe Asp Gly Tyr
        915                 920                 925
Asp Ser Thr Ala Pro Arg Leu Gly Arg Tyr Cys Gly Ser Gly Pro Pro
    930                 935                 940
Glu Glu Val Tyr Ser Ala Gly Asp Ser Val Leu Val Lys Phe His Ser
945                 950                 955                 960
Asp Asp Thr Ile Thr Lys Lys Gly Phe His Leu Arg Tyr Thr Ser Thr
                965                 970                 975
Lys Phe Gln Asp Thr Leu His Ser Arg Lys
            980                 985

<210> SEQ ID NO 3
<211> LENGTH: 2961
<212> TYPE: DNA
<213> ORGANISM: Homo sapiens

<400> SEQUENCE: 3
atgcccggcg tggcccgcct gccgctgctg ctcgggctgc tgctgctccc gcgtcccggc      60
cggccgctgg acttggccga ctacacctat gacctggcgg aggaggacga ctcggagccc     120
ctcaactaca agacccctg caaggcggct gcctttcttg ggacattgc cctgacgaa         180 gaggacctga gggccttcca ggtacagcag ctgtggatc tcagacggca cacagctcgt      240
aagtcctcca tcaaagctgc agttccagga aacacttcta cccccagctg ccagagcacc     300
aacgggcagc tcagaggggg agcctgtggg agatggagag gtagatcccg tagccggcgg     360
gcggcgacgt cccgaccaga gcgtgtgtgg cccgatgggg tcatcccctt tgtcattggg     420
ggaaacttca ctggtagcca gagggcagtc ttccggcagg ccatgaggca ctgggagaag     480
cacacctgtg tcaccttcct ggagcgcact gacgaggaca gctatattgt gttcaccta t    540 cgaccttgcg gtgctgctc ctacgtgggt cgccgcggcg ggggccccca ggccatctcc      600
```

```
atcggcaaga actgtgacaa gttcggcatt gtggtccacg agctgggcca cgtcgtcggc    660
ttctggcacg aacacactcg gccagaccgg gaccgccacg tttccatcgt tcgtgagaac    720
atccagccag ggcaggagta taacttcctg aagatggagc ctcaggaggt ggagtccctg    780
ggggagacct atgacttcga cagcatcatg cattacgctc ggaacacatt ctccaggggc    840
atcttcctgg ataccattgt ccccaagtat gaggtgaacg gggtgaaacc tcccattggc    900
caaaggacac ggctcagcaa gggggacatt gcccaagccc gcaagcttta caagtgccca    960
gcctgtggag agaccctgca agacagcaca ggcaacttct cctcccctga atacccaat    1020 ggctactctg ctcacatgca ctgcgtgtgg cgcatctctg tcacacccgg ggagaagatc   1080
atcctgaact tcacgtccct ggacctgtac cgcagccgcc tgtgctggta cgactatgtg   1140
gaggtccgag atggcttctg gaggaaggcg cccctccgag ccgcttctg cgggtccaaa    1200 ctccctgagc ctatcgtctc cactgacagc cgcctctggg ttgaattccg cagcagcagc   1260
aattgggttg gaaagggctt cttttgcagtc tacgaagcca tctgcggggg tgatgtgaaa   1320
aaggactatg ccacattca atcgcccaac tacccagacg attaccggcc cagcaaagtc   1380
tgcatctggc ggatccaggt gtctgagggc ttccacgtgg gcctcacatt ccagtccttt   1440
gagattgagc gccacgacag ctgtgcctac gactatctgg aggtgcgcga cgggcacagt   1500
gagagcagca ccctcatcgg gcgctactgt ggctatgaga gcctgatga catcaagagc   1560 acgtccagcc gcctctggct caagttcgtc tctgacgggt ccattaacaa agcgggcttt   1620
gccgtcaact ttttcaaaga ggtggacgag tgctctcggc caaccgcgg gggctgtgag   1680 cagcggtgcc tcaacacccct gggcagctac aagtgcagct gtgaccccgg gtacgagctg   1740
gccccagaca agcgccgctg tgaggctgct tgtggcggat tcctcaccaa gctcaacggc   1800
tccatcacca gcccgggctg gcccaaggag tacccccca caagaactg catctggcag   1860 ctggtggccc ccacccagta ccgcatctcc ctgcagtttg acttctttga dacagagggc   1920
aatgatgtgt gcaagtacga cttcgtggag gtgcgcagtg gactcacagc tgactccaag   1980
ctgcatggca agttctgtgg ttctgagaag cccgaggtca tcacctccca gtacaacaac   2040
atgcgcgtgg agttcaagtc cgacaacacc gtgtccaaaa agggcttcaa ggcccacttc   2100
ttctcagaca aggacgagtg ctccaaggat aacggcggct gccagcagga ctgcgtcaac   2160
acgttcggca gttatgagtg ccaatgccgc agtggcttcg tcctccatga caacaagcac   2220
gactgcaaag aagccggctg tgaccacaag gtgacatcca ccagtggtac catcaccagc   2280
cccaactggc ctgacaagta tcccagcaag aaggagtgca cgtgggccat ctccagcacc   2340
cccgggcacc gggtcaagct gaccttcatg gagatggaca tcgagtccca gcctgagtgt   2400
gcctacgacc acctagaggt gttcgacggg cgagacgcca aggcccccgt cctcggccgc   2460
ttctgtgggg caagaagcc cgagcccgtc tggccacag gcagccgcat gttcctgcgc   2520
ttctactcag ataactcggt ccagcgaaag ggcttccagg cctcccacgc cacagagtgc   2580
gggggccagt acgggcaga cgtgaagacc aaggaccttt actcccacgc ccagtttggc   2640
gacaacaact accctggggg tgtggactgt gagtgggtca ttgtggccga ggaaggctac   2700
ggcgtggagc tcgtgttcca gacctttgag gtggaggagg agaccgactg cggctatgac   2760
tacatggagc tcttcgacgg ctacgacagc acagcccca ggctggggcg ctactgtggc   2820
tcagggcctc ctgaggaggt gtactcggcg ggagattctg tcctggtgaa gttccactcg   2880
gatgacacca tcaccaaaaa aggtttccac ctgcgataca ccagcaccaa gttccaggac   2940
```
acactccaca gcaggaagtg a 2961

<210> SEQ ID NO 4
<211> LENGTH: 986
<212> TYPE: PRT
<213> ORGANISM: Homo sapiens

<400> SEQUENCE: 4

| Met | Pro | Gly | Val | Ala | Arg | Leu | Pro | Leu | Leu | Gly | Leu | Leu | Leu |
|---|---|---|---|---|---|---|---|---|---|---|---|---|---|
| 1 | | | | 5 | | | | | 10 | | | | 15 |

| Pro | Arg | Pro | Gly | Arg | Pro | Leu | Asp | Leu | Ala | Asp | Tyr | Thr | Tyr | Asp | Leu |
|---|---|---|---|---|---|---|---|---|---|---|---|---|---|---|---|
| | | | 20 | | | | | 25 | | | | | 30 | | |

Ala Glu Glu Asp Asp Ser Glu Pro Leu Asn Tyr Lys Asp Pro Cys Lys
                35                  40                  45

Ala Ala Ala Phe Leu Gly Asp Ile Ala Leu Asp Glu Glu Asp Leu Arg
        50                  55                  60

Ala Phe Gln Val Gln Gln Ala Val Asp Leu Arg Arg His Thr Ala Arg
65                  70                  75                  80

Lys Ser Ser Ile Lys Ala Ala Val Pro Gly Asn Thr Ser Thr Pro Ser
                85                  90                  95

Cys Gln Ser Thr Asn Gly Gln Pro Gln Arg Gly Ala Cys Gly Arg Trp
            100                 105                 110

Arg Gly Arg Ser Arg Ser Arg Arg Ala Ala Thr Ser Arg Pro Glu Arg
        115                 120                 125

Val Trp Pro Asp Gly Val Ile Pro Phe Val Ile Gly Gly Asn Phe Thr
    130                 135                 140

Gly Ser Gln Arg Ala Val Phe Arg Gln Ala Met Arg His Trp Glu Lys
145                 150                 155                 160

His Thr Cys Val Thr Phe Leu Glu Arg Thr Asp Glu Asp Ser Tyr Ile
                165                 170                 175

Val Phe Thr Tyr Arg Pro Cys Gly Cys Cys Ser Tyr Val Gly Arg Arg
            180                 185                 190

Gly Gly Gly Pro Gln Ala Ile Ser Ile Gly Lys Asn Cys Asp Lys Phe
        195                 200                 205

Gly Ile Val Val His Glu Leu Gly His Val Val Gly Phe Trp His Glu
    210                 215                 220

His Thr Arg Pro Asp Arg Asp Arg His Val Ser Ile Val Arg Glu Asn
225                 230                 235                 240

Ile Gln Pro Gly Gln Glu Tyr Asn Phe Leu Lys Met Glu Pro Gln Glu
                245                 250                 255

Val Glu Ser Leu Gly Glu Thr Tyr Asp Phe Asp Ser Ile Met His Tyr
            260                 265                 270

Ala Arg Asn Thr Phe Ser Arg Gly Ile Phe Leu Asp Thr Ile Val Pro
        275                 280                 285

Lys Tyr Glu Val Asn Gly Val Lys Pro Pro Ile Gly Gln Arg Thr Arg
    290                 295                 300

Leu Ser Lys Gly Asp Ile Ala Gln Ala Arg Lys Leu Tyr Lys Cys Pro
305                 310                 315                 320

Ala Cys Gly Glu Thr Leu Gln Asp Ser Thr Gly Asn Phe Ser Ser Pro
                325                 330                 335

Glu Tyr Pro Asn Gly Tyr Ser Ala His Met His Cys Val Trp Arg Ile
            340                 345                 350

Ser Val Thr Pro Gly Glu Lys Ile Ile Leu Asn Phe Thr Ser Leu Asp
        355                 360                 365

```
Leu Tyr Arg Ser Arg Leu Cys Trp Tyr Asp Tyr Val Glu Val Arg Asp
        370                 375                 380

Gly Phe Trp Arg Lys Ala Pro Leu Arg Gly Arg Phe Cys Gly Ser Lys
385                 390                 395                 400

Leu Pro Glu Pro Ile Val Ser Thr Asp Ser Arg Leu Trp Val Glu Phe
                405                 410                 415

Arg Ser Ser Asn Trp Val Gly Lys Gly Phe Phe Ala Val Tyr Glu
                420                 425                 430

Ala Ile Cys Gly Gly Asp Val Lys Lys Asp Tyr Gly His Ile Gln Ser
                435                 440                 445

Pro Asn Tyr Pro Asp Asp Tyr Arg Pro Ser Lys Val Cys Ile Trp Arg
        450                 455                 460

Ile Gln Val Ser Glu Gly Phe His Val Gly Leu Thr Phe Gln Ser Phe
465                 470                 475                 480

Glu Ile Glu Arg His Asp Ser Cys Ala Tyr Asp Tyr Gln Glu Val Arg
                485                 490                 495

Asp Gly His Ser Glu Ser Ser Thr Leu Ile Gly Arg Tyr Cys Gly Tyr
                500                 505                 510

Glu Lys Pro Asp Asp Ile Lys Ser Thr Ser Ser Arg Leu Trp Leu Lys
                515                 520                 525

Phe Val Ser Asp Gly Ser Ile Asn Lys Ala Gly Phe Ala Val Asn Phe
530                 535                 540

Phe Lys Glu Val Asp Glu Cys Ser Arg Pro Asn Arg Gly Gly Cys Glu
545                 550                 555                 560

Gln Arg Cys Leu Asn Thr Leu Gly Ser Tyr Lys Cys Ser Cys Asp Pro
                565                 570                 575

Gly Tyr Glu Leu Ala Pro Asp Lys Arg Arg Cys Glu Ala Ala Cys Gly
                580                 585                 590

Gly Phe Leu Thr Lys Leu Asn Gly Ser Ile Thr Ser Pro Gly Trp Pro
        595                 600                 605

Lys Glu Tyr Pro Pro Asn Lys Asn Cys Ile Trp Gln Leu Val Ala Pro
610                 615                 620

Thr Gln Tyr Arg Ile Ser Leu Gln Phe Asp Phe Phe Glu Thr Glu Gly
625                 630                 635                 640

Asn Asp Val Cys Lys Tyr Asp Phe Val Glu Val Arg Ser Gly Leu Thr
                645                 650                 655

Ala Asp Ser Lys Leu His Gly Lys Phe Cys Gly Ser Glu Lys Pro Glu
                660                 665                 670

Val Ile Thr Ser Gln Tyr Asn Asn Met Arg Val Glu Phe Lys Ser Asp
        675                 680                 685

Asn Thr Val Ser Lys Lys Gly Phe Lys Ala His Phe Ser Asp Lys
        690                 695                 700

Asp Glu Cys Ser Lys Asp Asn Gly Gly Cys Gln Gln Asp Cys Val Asn
705                 710                 715                 720

Thr Phe Gly Ser Tyr Glu Cys Gln Cys Arg Ser Gly Phe Val Leu His
                725                 730                 735

Asp Asn Lys His Asp Cys Lys Glu Ala Gly Cys Asp His Lys Val Thr
                740                 745                 750

Ser Thr Ser Gly Thr Ile Thr Ser Pro Asn Trp Pro Asp Lys Tyr Pro
        755                 760                 765

Ser Lys Lys Glu Cys Thr Trp Ala Ile Ser Ser Thr Pro Gly His Arg
770                 775                 780

Val Lys Leu Thr Phe Met Glu Met Asp Ile Glu Ser Gln Pro Glu Cys
```

```
                785                 790                 795                 800
Ala Tyr Asp His Leu Glu Val Phe Asp Gly Arg Asp Ala Lys Ala Pro
                805                 810                 815

Val Leu Gly Arg Phe Cys Gly Ser Lys Lys Pro Glu Pro Val Leu Ala
                820                 825                 830

Thr Gly Ser Arg Met Phe Leu Arg Phe Tyr Ser Asp Asn Ser Val Gln
                835                 840                 845

Arg Lys Gly Phe Gln Ala Ser His Ala Thr Glu Cys Gly Gly Gln Val
                850                 855                 860

Arg Ala Asp Val Lys Thr Lys Asp Leu Tyr Ser His Ala Gln Phe Gly
865                 870                 875                 880

Asp Asn Asn Tyr Pro Gly Gly Val Asp Cys Glu Trp Val Ile Val Ala
                885                 890                 895

Glu Glu Gly Tyr Gly Val Glu Leu Val Phe Gln Thr Phe Glu Val Glu
                900                 905                 910

Glu Glu Thr Asp Cys Gly Tyr Asp Tyr Met Glu Leu Phe Asp Gly Tyr
                915                 920                 925

Asp Ser Thr Ala Pro Arg Leu Gly Arg Tyr Cys Gly Ser Gly Pro Pro
                930                 935                 940

Glu Glu Val Tyr Ser Ala Gly Asp Ser Val Leu Val Lys Phe His Ser
945                 950                 955                 960

Asp Asp Thr Ile Thr Lys Lys Gly Phe His Leu Arg Tyr Thr Ser Thr
                965                 970                 975

Lys Phe Gln Asp Thr Leu His Ser Arg Lys
                980                 985

<210> SEQ ID NO 5
<211> LENGTH: 2961
<212> TYPE: DNA
<213> ORGANISM: Homo sapiens

<400> SEQUENCE: 5
atgcccggcg tggcccgcct gccgctgctg ctcgggctgc tgctgctccc gcgtcccggc        60
cggccgctgg acttggccga ctacacctat gacctggcgg aggaggacga ctcggagccc       120
ctcaactaca agaccccctg caaggcggct gcctttcttg gggacattgc cctggacgaa       180
gaggacctga gggccttcca ggtacagcag gctgtggatc tcagacggca cacagctcgt       240
aagtcctcca tcaaagctgc agttccagga aacacttcta cccccagctg ccagagcacc       300
aacgggcagc tcagaggggg agcctgtggg agatggagag tagatcccg tagccggcgg       360 gcggcgacgt cccgaccaga gcgtgtgtgg cccgatgggg tcatcccctt tgtcattggg       420
ggaaacttca ctggtagcca gagggcagtc ttccggcagg ccatgaggca ctgggagaag       480
cacacctgtg tcaccttcct ggagcgcact gacgaggaca gctatattgt gttcacctat       540
cgaccttgcg ggtgctgctc ctacgtgggt cgccgcggcg ggggccccca ggccatctcc       600
atcggcaaga actgtgacaa gttcggcatt gtggtccacg agctgggcca cgtcgtcggc       660
ttctggcacg aacacactcg gccagaccgg gaccgccacg tttccatcgt tcgtgagaac       720
atccagccag gcaggagta taacttcctg aagatggagc tcaggaggt ggagtccctg       780 ggggagacct atgacttcga cagcatcatg cattacgctc ggaacacatt ctccaggggc       840
atcttcctgg ataccattgt ccccaagtat gaggtgaacg ggtgaaacc tccattggc       900 caaaggacac ggctcagcaa ggggacatt gcccaagccc gcaagcttta caagtgccca       960
gcctgtggag agaccctgca agacagcaca ggcaacttct cctcccctga atacccaat      1020
```

-continued

```
ggctactctg ctcacatgca ctgcgtgtgg cgcatctctg tcacacccgg ggagaagatc    1080
atcctgaact tcacgtccct ggacctgtac cgcagccgcc tgtgctggta cgactatgtg    1140
gaggtccgag atggcttctg gaggaaggcg cccctccgag ccgcttctg cgggtccaaa     1200 ctccctgagc ctatcgtctc cactgacagc cgcctctggg ttgaattccg cagcagcagc    1260 aattggggttg gaaagggctt cttttgcagtc tacgaagcca tctgcggggg tgatgtgaaa   1320
aaggactatg ccacattca atcgcccaac tacccagacg attaccggcc cagcaaagtc    1380
tgcatctggc ggatccaggt gtctgagggc ttccacgtgg cctcacatt ccagtccttt     1440 gagattgagc gccacgacag ctgtgcctac gactatcagg aggtgcgcga cgggcacagt    1500
gagagcagca ccctcatcgg gcgctactgt ggctatgaga agcctgatga catcaagagc    1560
acgtccagcc gcctctggct caagttcgtc tctgacgggt ccattaacaa agcgggcttt    1620
gccgtcaact ttttcaaaga ggtggacgag tgctctcggc caaccgcgg gggctgtgag     1680 cagcggtgcc tcaacaccct gggcagctac aagtgcagct gtgaccccgg gtacgagctg    1740
gccccagaca agcgccgctg tgaggctgct tgtggcggat cctcaccaa gctcaacggc     1800 tccatcacca gcccgggctg gcccaaggag taccccccca acaagaactg catctggcag    1860
ctggtgcccc ccacccagta ccgcatctcc ctgcagtttg acttctttga cacagagggc    1920
aatgatgtgt gcaagtacga cttcgtggag gtgcgcagtg gactcacagc tgactccaag    1980
ctgcatggca agttctgtgg ttctgagaag cccgaggtca tcacctccca gtacaacaac    2040
atgcgcgtgg agttcaagtc cgacaacacc gtgtccaaaa agggcttcaa ggcccacttc    2100
ttctcagaca aggacgagtg ctccaaggat aacggcggct ccagcagga ctgcgtcaac     2160 acgttcggca gttatgagtg ccaatgccgc agtggcttcg tcctccatga caacaagcac    2220
gactgcaaag aagccggctg tgaccacaag gtgacatcca ccagtggtac catcaccagc    2280
cccaactggc tgacaagta tcccagcaag aaggagtgca cgtgggccat ctccagcacc    2340
cccgggcacc gggtcaagct gaccttcatg gagatggaca tcgagtccca gctgagtgt    2400 gcctacgacc acctagaggt gttcgacggg cgagacgcca aggccccgt cctcggccgc     2460 ttctgtggga gcaagaagcc cgagcccgtc ctggccacag gcagccgcat gttcctgcgc    2520
ttctactcag ataactcggt ccagcgaaag ggcttccagg cctccacgc cacagagtgc    2580 gggggccagg tacgggcaga cgtgaagacc aaggaccttt actcccacgc ccagtttggc    2640
gacaacaact cccctgggggg tgtggactgt gagtgggtca ttgtggccga ggaaggctac    2700
ggcgtggagc tcgtgttcca gacctttgag gtggaggagg agaccgactg cggctatgac    2760
tacatggagc tcttcgacgg ctacgacagc acagcccccca ggctggggcg ctactgtggc    2820
tcagggcctc ctgaggaggt gtactcggcg ggagattctg tcctggtgaa gttccactcg    2880
gatgacacca tcaccaaaaa aggtttccac ctgcgataca ccagcaccaa gttccaggac    2940
acactccaca gcaggaagtg a                                              2961
```

<210> SEQ ID NO 6
<211> LENGTH: 622
<212> TYPE: PRT
<213> ORGANISM: Homo sapiens

<400> SEQUENCE: 6

Met Pro Gly Val Ala Arg Leu Pro Leu Leu Gly Leu Leu Leu Leu
1               5                   10                  15

Pro Arg Pro Gly Arg Pro Leu Asp Leu Ala Asp Tyr Thr Tyr Asp Leu

-continued

```
                 20                  25                  30
Ala Glu Glu Asp Asp Ser Glu Pro Leu Asn Tyr Lys Asp Pro Cys Lys
            35                  40                  45
Ala Ala Ala Phe Leu Gly Asp Ile Ala Leu Asp Glu Glu Asp Leu Arg
50                  55                  60
Ala Phe Gln Val Gln Gln Ala Val Asp Leu Arg Arg His Thr Ala Arg
65                  70                  75                  80
Lys Ser Ser Ile Lys Ala Ala Val Pro Gly Asn Thr Ser Thr Pro Ser
                85                  90                  95
Cys Gln Ser Thr Asn Gly Gln Pro Gln Arg Gly Ala Cys Gly Arg Trp
            100                 105                 110
Arg Gly Arg Ser Arg Ser Arg Arg Ala Ala Thr Ser Arg Pro Glu Arg
        115                 120                 125
Val Trp Pro Asp Gly Val Ile Pro Phe Val Ile Gly Gly Asn Phe Thr
    130                 135                 140
Gly Ser Gln Arg Ala Val Phe Arg Gln Ala Met Arg His Trp Glu Lys
145                 150                 155                 160
His Thr Cys Val Thr Phe Leu Glu Arg Thr Asp Glu Asp Ser Tyr Ile
                165                 170                 175
Val Phe Thr Tyr Arg Pro Cys Gly Cys Cys Ser Tyr Val Gly Arg Arg
            180                 185                 190
Gly Gly Gly Pro Gln Ala Ile Ser Ile Gly Lys Asn Cys Asp Lys Phe
        195                 200                 205
Gly Ile Val Val His Glu Leu Gly His Val Val Gly Phe Trp His Glu
    210                 215                 220
His Thr Arg Pro Asp Arg Asp Arg His Val Ser Ile Val Arg Glu Asn
225                 230                 235                 240
Ile Gln Pro Gly Gln Glu Tyr Asn Phe Leu Lys Met Glu Pro Gln Glu
                245                 250                 255
Val Glu Ser Leu Gly Glu Thr Tyr Asp Phe Asp Ser Ile Met His Tyr
            260                 265                 270
Ala Arg Asn Thr Phe Ser Arg Gly Ile Phe Leu Asp Thr Ile Val Pro
        275                 280                 285
Lys Tyr Glu Val Asn Gly Val Lys Pro Pro Ile Gly Gln Arg Thr Arg
    290                 295                 300
Leu Ser Lys Gly Asp Ile Ala Gln Ala Arg Lys Leu Tyr Lys Cys Pro
305                 310                 315                 320
Ala Cys Gly Glu Thr Leu Gln Asp Ser Thr Gly Asn Phe Ser Ser Pro
                325                 330                 335
Glu Tyr Pro Asn Gly Tyr Ser Ala His Met His Cys Val Trp Arg Ile
            340                 345                 350
Ser Val Thr Pro Gly Glu Lys Ile Ile Leu Asn Phe Thr Ser Leu Asp
        355                 360                 365
Leu Tyr Arg Ser Arg Leu Cys Trp Tyr Asp Tyr Val Glu Val Arg Asp
    370                 375                 380
Gly Phe Trp Arg Lys Ala Pro Leu Arg Gly Arg Phe Cys Gly Ser Lys
385                 390                 395                 400
Leu Pro Glu Pro Ile Val Ser Thr Asp Ser Arg Leu Trp Val Glu Phe
                405                 410                 415
Arg Ser Ser Ser Asn Trp Val Gly Lys Gly Phe Phe Ala Val Tyr Glu
            420                 425                 430
Ala Ile Cys Gly Gly Asp Val Lys Lys Asp Tyr Gly His Ile Gln Ser
        435                 440                 445
```

```
Pro Asn Tyr Pro Asp Asp Tyr Arg Pro Ser Lys Val Cys Ile Trp Arg
    450                 455                 460

Ile Gln Val Ser Glu Gly Phe His Val Gly Leu Thr Phe Gln Ser Phe
465                 470                 475                 480

Glu Ile Glu Arg His Asp Ser Cys Ala Tyr Asp Tyr Leu Glu Val Arg
                485                 490                 495

Asp Gly His Ser Glu Ser Ser Thr Leu Ile Gly Arg Tyr Cys Gly Tyr
                500                 505                 510

Glu Lys Pro Asp Asp Ile Lys Ser Thr Ser Ser Arg Leu Trp Leu Lys
            515                 520                 525

Phe Val Ser Asp Gly Ser Ile Asn Lys Ala Gly Phe Ala Val Asn Phe
        530                 535                 540

Phe Lys Glu Val Asp Glu Cys Ser Arg Pro Asn Arg Gly Gly Cys Glu
545                 550                 555                 560

Gln Arg Cys Leu Asn Thr Leu Gly Ser Tyr Lys Cys Ser Cys Asp Pro
                565                 570                 575

Gly Tyr Glu Leu Ala Pro Asp Lys Arg Arg Cys Glu Gly Cys Tyr Asp
                580                 585                 590

Leu Gln Val Gly Lys Pro Leu Leu Trp Asp Arg His Cys Phe Arg Leu
            595                 600                 605

Ser Thr His Gly Pro Glu Met Leu Gly Thr Ala Leu Arg Gly
        610                 615                 620

<210> SEQ ID NO 7
<211> LENGTH: 823
<212> TYPE: PRT
<213> ORGANISM: Homo sapiens

<400> SEQUENCE: 7

Met Pro Gly Val Ala Arg Leu Pro Leu Leu Gly Leu Leu Leu Leu Leu
1               5                   10                  15

Pro Arg Pro Gly Arg Pro Leu Asp Leu Ala Asp Tyr Thr Tyr Asp Leu
                20                  25                  30

Ala Glu Glu Asp Asp Ser Glu Pro Leu Asn Tyr Lys Asp Pro Cys Lys
            35                  40                  45

Ala Ala Ala Phe Leu Gly Asp Ile Ala Leu Asp Glu Glu Asp Leu Arg
        50                  55                  60

Ala Phe Gln Val Gln Gln Ala Val Asp Leu Arg Arg His Thr Ala Arg
65                  70                  75                  80

Lys Ser Ser Ile Lys Ala Ala Val Pro Gly Asn Thr Ser Thr Pro Ser
                85                  90                  95

Cys Gln Ser Thr Asn Gly Gln Pro Gln Arg Gly Ala Cys Gly Arg Trp
                100                 105                 110

Arg Gly Arg Ser Arg Ser Arg Arg Ala Ala Thr Ser Arg Pro Glu Arg
            115                 120                 125

Val Trp Pro Asp Gly Val Ile Pro Phe Val Ile Gly Gly Asn Phe Thr
        130                 135                 140

Gly Ser Gln Arg Ala Val Phe Arg Gln Ala Met Arg His Trp Glu Lys
145                 150                 155                 160

His Thr Cys Val Thr Phe Leu Glu Arg Thr Asp Glu Asp Ser Tyr Ile
                165                 170                 175

Val Phe Thr Tyr Arg Pro Cys Gly Cys Cys Ser Tyr Val Gly Arg Arg
                180                 185                 190

Gly Gly Gly Pro Gln Ala Ile Ser Ile Gly Lys Asn Cys Asp Lys Phe
```

-continued

```
           195                200                205
Gly Ile Val Val His Glu Leu Gly His Val Gly Phe Trp His Glu
210                 215                 220
His Thr Arg Pro Asp Arg Asp Arg His Val Ser Ile Val Arg Glu Asn
225                 230                 235                 240
Ile Gln Pro Gly Gln Glu Tyr Asn Phe Leu Lys Met Glu Pro Gln Glu
                245                 250                 255
Val Glu Ser Leu Gly Glu Thr Tyr Asp Phe Asp Ser Ile Met His Tyr
            260                 265                 270
Ala Arg Asn Thr Phe Ser Arg Gly Ile Phe Leu Asp Thr Ile Val Pro
        275                 280                 285
Lys Tyr Glu Val Asn Gly Val Lys Pro Pro Ile Gly Gln Arg Thr Arg
290                 295                 300
Leu Ser Lys Gly Asp Ile Ala Gln Ala Arg Lys Leu Tyr Lys Cys Pro
305                 310                 315                 320
Ala Cys Gly Glu Thr Leu Gln Asp Ser Thr Gly Asn Phe Ser Ser Pro
                325                 330                 335
Glu Tyr Pro Asn Gly Tyr Ser Ala His Met His Cys Val Trp Arg Ile
            340                 345                 350
Ser Val Thr Pro Gly Glu Lys Ile Ile Leu Asn Phe Thr Ser Leu Asp
        355                 360                 365
Leu Tyr Arg Ser Arg Leu Cys Trp Tyr Asp Tyr Val Glu Val Arg Asp
370                 375                 380
Gly Phe Trp Arg Lys Ala Pro Leu Arg Gly Arg Phe Cys Gly Ser Lys
385                 390                 395                 400
Leu Pro Glu Pro Ile Val Ser Thr Asp Ser Arg Leu Trp Val Glu Phe
                405                 410                 415
Arg Ser Ser Ser Asn Trp Val Gly Lys Gly Phe Phe Ala Val Tyr Glu
            420                 425                 430
Ala Ile Cys Gly Gly Asp Val Lys Asp Tyr Gly His Ile Gln Ser
        435                 440                 445
Pro Asn Tyr Pro Asp Asp Tyr Arg Pro Ser Lys Val Cys Ile Trp Arg
450                 455                 460
Ile Gln Val Ser Glu Gly Phe His Val Gly Leu Thr Phe Gln Ser Phe
465                 470                 475                 480
Glu Ile Glu Arg His Asp Ser Cys Ala Tyr Asp Tyr Leu Glu Val Arg
                485                 490                 495
Asp Gly His Ser Glu Ser Ser Thr Leu Ile Gly Arg Tyr Cys Gly Tyr
            500                 505                 510
Glu Lys Pro Asp Asp Ile Lys Ser Thr Ser Ser Arg Leu Trp Leu Lys
        515                 520                 525
Phe Val Ser Asp Gly Ser Ile Asn Lys Ala Gly Phe Ala Val Asn Phe
530                 535                 540
Phe Lys Glu Val Asp Glu Cys Ser Arg Pro Asn Arg Gly Gly Cys Glu
545                 550                 555                 560
Gln Arg Cys Leu Asn Thr Leu Gly Ser Tyr Lys Cys Ser Cys Asp Pro
                565                 570                 575
Gly Tyr Glu Leu Ala Pro Asp Lys Arg Arg Cys Glu Ala Ala Cys Gly
            580                 585                 590
Gly Phe Leu Thr Lys Leu Asn Gly Ser Ile Thr Ser Pro Gly Trp Pro
        595                 600                 605
Lys Glu Tyr Pro Pro Asn Lys Asn Cys Ile Trp Gln Leu Val Ala Pro
610                 615                 620
```

```
Thr Gln Tyr Arg Ile Ser Leu Gln Phe Asp Phe Phe Glu Thr Glu Gly
625                 630                 635                 640

Asn Asp Val Cys Lys Tyr Asp Phe Val Glu Val Arg Ser Gly Leu Thr
                645                 650                 655

Ala Asp Ser Lys Leu His Gly Lys Phe Cys Gly Ser Glu Lys Pro Glu
            660                 665                 670

Val Ile Thr Ser Gln Tyr Asn Asn Met Arg Val Glu Phe Lys Ser Asp
        675                 680                 685

Asn Thr Val Ser Lys Lys Gly Phe Lys Ala His Phe Phe Ser Val Leu
    690                 695                 700

Glu Gly Ala Gly Asp Arg His Ser His Leu Ser Gly Leu Glu Leu Leu
705                 710                 715                 720

Leu Cys Pro His Ala Leu Val Asp Thr Val Pro Ala Pro Pro Ser Ala
                725                 730                 735

Leu His Gly Asp Thr His Ala His Thr His Thr His Val His Thr His
                740                 745                 750

Cys Pro Ile Ala Gln Glu Thr Cys Arg Gly Pro Pro Leu Gly Ala Ser
            755                 760                 765

Arg Leu Ser Pro Gln Gly Pro Gly His Leu Thr Leu Ala Pro Gln Glu
    770                 775                 780

Gly Ser Tyr Leu Asp Phe Trp Asp Thr His Arg Gly Asp Pro Lys Pro
785                 790                 795                 800

Arg Arg Arg Arg Lys Ser Leu Lys Thr Phe Ser Leu Thr Pro Ala Thr
                805                 810                 815

Phe Arg Gly Ile Trp Ala Leu
                820
```

BMP-1 PROCOLLAGEN C-PROTEINASE FOR DIAGNOSIS AND TREATMENT OF BONE AND SOFT TISSUE DEFECTS AND DISORDERS

RELATED APPLICATIONS

This application is a United States national stage filing under 35 U.S.C. §371 of international application No. PCT/US2007/016605, filed Jul. 23, 2007, designating the U.S., which claims priority to U.S. Provisional Application No. 60/832,325, filed Jul. 21, 2006.

FIELD OF THE INVENTION

This invention is in the field of diagnosis and regeneration of tissue defects and disorders. In particular, the invention provides compositions and methods comprising isoforms of BMP-1 to diagnose and treat tissue defects and disorders.

BACKGROUND

Bone morphogenetic proteins (BMPs) are bone-inducing (osteogenic, osteoinductive) molecules that have been purified and characterized from bone (Sampath and Reddi, *Proc. Natl. Acad. Sci. USA*, 78: 7599 (1981)). The term "bone morphogenetic protein", "BMP", and "morphogen" are synonymous and refer to members of a particular subclass (i.e., the BMP family) of the transforming growth factor-β (TGF-β) superfamily of proteins (see, e.g., Hoffmann et al., *Appl. Microbiol. Biotechnol*, 57: 294-308 (2001); Reddi, *J. Bone Joint Surg.*, 83-A(Supp. 1): S1-S6 (2001); U.S. Pat. Nos. 4,968,590; 5,011,691; 5,674,844; 6,333,312). All such BMPs have a signal peptide, prodomain, and a carboxy-terminal (mature) domain. The carboxy-terminal domain is the mature form of the BMP monomer and contains a highly conserved region characterized by seven cysteines that form a cysteine knot (see, Griffith et al., *Proc. Natl. Acad. Sci. USA*, 93: 878-883 (1996)). BMPs were originally isolated from mammalian bone using protein purification methods (see, e.g., Urist et al., *Proc. Soc. Exp. Biol. Med.*, 173: 194-199 (1983); Urist et al., *Proc. Natl. Acad. Sci. USA*, 81: 371-375 (1987); Sampath et al., *Proc. Natl. Acad. Sci. USA*, 84: 7109-7113 (1987); U.S. Pat. No. 5,496,552). However, BMPs have also been detected in or isolated from a variety of other mammalian tissues and organs such as kidney, liver, lung, brain, muscle, teeth, and gut. Most BMPs (including BMP-2, BMP-4, BMP-6, BMP-7, BMP-9, BMP-12, BMP-13) also stimulate cartilage and bone formation as demonstrated in a standard ectopic assay for bone formation (see, e.g., Sampath and Reddi, *Proc. Natl. Acad. Sci. USA*, 80: 6591-6595 (1983)). Accordingly, such authentic BMPs are also referred to as "osteogenic" even though they may also promote soft tissue regeneration.

The protein referred to routinely as BMP-1 is not an authentic member of the BMP family of osteogenic, tissue regenerative proteins. BMP-1 was originally isolated from highly purified BMP bovine bone extracts and was originally reported to induce the formation of cartilage in vivo in a subcutaneous (ectopic) bone formation assay (Wozney et al., *Science*, 242: 1528 (1988)). However, BMP-1 does not share significant amino acid sequence homology with other BMPs, nor does BMP-1 exhibit the characteristic signal peptide, prodomain, carboxy-terminal (mature domain), or cysteine knot found in other BMPs. In fact, BMP-1 was shown to be identical to procollagen C-proteinase, an enzyme essential for the proper assembly of collagen within the extracellular matrix (ECM) (Kessler et al., *Science*, 271: 360-362 (1996)). The erroneous status of BMP-1 within the TGF-β family resulted from flaws in the original bioassay for osteogenesis (Wozney et al., op. cit.) in which the cartilage observed in the bioassay appears to have been old growth plate cartilage contaminating the insoluble bone matrix that was misidentified as newly formed tissue (see, Reddi, *Science*, 271: 463 (1996)). As shown herein, unlike authentic osteogenic BMPs, the BMP-1-1 isoform does not induce cartilage or bone formation in a standard ectopic bone formation assay.

The BMP-1 gene is related to the *Drosophila* gene tolloid (TLD), which is implicated in the patterning controlled by the decapentaplegic (DPP) gene by virtue of its ability to activate TGF-β-like morphogens. The BMP-1 protein is now known to be an essential control point of morphogenesis during the cascade of pattern formation (Ge and Greenspan, *Birth Defect Res.*, 78: 47-68 (2006)).

BMP-1 is the prototype of a small subgroup of metalloproteinases found in a broad range of species. In mammals, there are four BMP-1/TLD-related (or BMP-1/TLD-like) metalloproteinases. The gene encoding BMP-1 also encodes a second, longer proteinase that is encoded by alternatively spliced mRNA. With a domain structure that is essentially identical to TLD, this proteinase was designated mammalian Tolloid (mTLD) (Takahara et al., *J. Biol. Chem.*, 269: 32572-32578 (1994)). In addition, there are two genetically distinct mammalian BMP-1/TLD-related proteinases, designated mammalian Tolloid-like 1 and 2 (mTLL1 and mTLL2). The prodomains of BMP-1/TLD-like proteinases must be proteolytically removed by subtilisin-like proprotein convertases (SPCs) (Leighton and Kadler, *J. Biol. Chem.*, 278: 18478-18484 (2003)) to achieve full activity of these proteinases. The role of the prodomain of BMP-1/TLD-like proteinases appears to be in maintaining the BMP-1/TLD-like proteinases in a latent form (Marques et al., *Cell*, 91: 417-426 (1997); Sieron et al., *Biochem.*, 39: 3231-3239 (2000); Leighton and Kadler, op. cit.).

BMP-1/TLD-related metalloproteinases are responsible for the proteolytic maturation of a number of extracellular proteins related to formation of the extracellular matrix (ECM). These include various collagens, small leucine-rich proteoglycans, SIBLING proteins, and the enzyme lysyl oxidases, laminin-5, and an anti-angiogenic factor from the basement membrane proteoglycan perlecan (Iozzo, *Nat. Rev. Mol. Cell. Biol.*, 6: 646-656 (2005); Greenspan, *Top. Curr. Chem.*, 247: 149-183 (2005); Ge and Greenspan *Birth Defect Res.*, op. cit.). BMP-1 is also involved in releasing BMPs from extracellular matrix or in activating latent TGF-β family members, such as BMP-4, BMP-11 and GDF-8 (Wolfman et al., *Proc. Natl. Acad. Sci. USA*, 100: 15842-15846 (2003); Ge et al, *Mol. Cell. Biol.*, 25: 5846-5858 (2005)).

The originally discovered form of BMP-1 is designated as BMP-1-1, and other BMP-1 isoforms encoded by splice variant RNA transcripts have been described on the transcriptional level and designated with sequential suffixes: BMP-1-2, BMP-1-3, BMP-1-4, BMP-1-5, BMP-1-6, and BMP-1-7 (Li et al., *Proc. Natl. Acad. Sci. USA*, 93: 5127-5131 (1996); Wozney et al., *Science*, 242:1528 (1988); Janitz et al., *J. Mol. Med.*, 76:141 (1998); Takahara et al *J. Biol. Chem.*, 269: 32572 (1994); Hillman et al., *Genome Biol.*, 5: 16 (2004). As expected, the BMP-1 isoforms encoded by the splice variant transcripts share a number of domains, including leader peptide, proregion, and protease (catalytic) region. Only the original BMP-1, i.e., BMP-1-1, has previously been confirmed on the protein level following its isolation from bone. The sequences for BMP-1-2 and other BMP-1 isoforms were deduced from nucleotide sequences of the splice variant transcripts, but have not been described at the protein level.

Despite the correction in the literature of the identity of BMP-1-1, whether this protein or other BMP-1 isoforms have any role of therapeutic relevance remains to be elucidated.

SUMMARY OF THE INVENTION

The present invention provides new methods of diagnosis and therapy based on discoveries relating to the circulation of BMP-1 isoforms in the blood of individuals. The differential appearance of particular isoforms in the circulating blood of individuals has now been associated with particular bone defects or disorders of soft tissue. Accordingly, it is now possible for early diagnosis of particular disorders such as acute bone fracture, chronic renal failure, fibrodysplasia ossificans progressive, osteogenesis imperfecta, acute pancreatitis, and liver cirrhosis using a simple blood test to detect the presence of one or more BMP-1 isoforms in a sample of blood. Moreover, the discoveries disclosed herein have led to the development of new treatment methods which enhance the effects of osteogenic bone morphogenic proteins (BMPs) in individuals suffering from particular bone defects. (See, Example 14, below.)

One embodiment of the present invention involves a method of diagnosing a defect or disorder in a bone or soft tissue of an individual comprising determining the profile of BMP-1 isoforms in the blood of the individual and comparing the profile to a standard blood profile of BMP-1 isoforms associated with various defects and disorders. Such a standard blood profile based on pooled blood from healthy individuals and individuals undergoing treatment for various bone and soft tissue disorders is presented in Table 1 (infra).

The diagnostic methods of the present invention are advantageously carried out using detector molecules capable of binding to one or more BMP-1 isoforms. Suitable such detector molecules include antibody molecules (including polyclonal antibodies and monoclonal antibodies, and binding fragments of antibodies such as Fab fragments, F(ab')$_2$ fragments, and the like) and aptamers (i.e., nucleic acid molecules that have a specific binding affinity for particular proteins).

Thus, in a particular embodiment for diagnostic methods of the invention, a blood isoform profile for an individual is made, using one or more detector molecules to assay a sample of blood from the individual for the presence of one or more BMP-1 isoforms. Circulating BMP-1 isoforms, or the complete absence of any circulating isoforms, is demonstrated herein to be indicative of particular disorders. The ability to detect these defects or disorders from a blood sample is advantageous because a positive diagnosis can be achieved much earlier in the course of the disorder. Acute pancreatitis, for example, may be detected from the presence of circulating BMP-1-7 and may be diagnosed prior to the manifestation of more overt symptoms of the disease. Similarly, an acute bone fracture such as a hairline fracture or crack that is not easily detectable (or not detectable without expensive x-rays) may be deduced in the first instance using a blood test and observing the complete absence of BMP-1 isoforms. In particular embodiments, detector molecules such as antibody molecules or aptamers specific for one or more BMP-1 isoforms are used in an assay to detect the presence of one or more BMP-1 isoforms in a sample of blood, and the presence of certain isoforms (or the complete absence of isoforms) is indicative of a disorder associated with such presence (or absence) herein.

Preferred detector molecules for the diagnostic methods of this invention are monoclonal antibody molecules. A suitable anti-BMP-1 isoform antibody molecule for use herein may be an immunoglobulin, a Fab fragment, a F(ab')$_2$ molecule, a single chain antibody molecule (scFv), a double scFv molecule, a single domain antibody molecule (dAb), a Fd molecule, a diabody molecule, a fusion protein comprising any of said antibody molecules, or combinations of one or more of the foregoing.

In a particular method according to the present invention, a method is provided for diagnosing liver cirrhosis in an individual comprising: testing a blood sample from an individual to determine the presence in the sample of the BMP-1 isoforms BMP-1-1, BMP-1-3, BMP-1-5, and BMP-1-7, wherein the absence of said BMP-1 isoforms in the sample is indicative of liver cirrhosis in the individual.

Another particular embodiment of the present invention is a method for diagnosing acute bone fracture in an individual comprising: testing a blood sample from an individual to determine the presence in the sample of the BMP-1 isoforms BMP-1-1, BMP-1-3, BMP-1-5, and BMP-1-7, wherein the absence of said BMP-1 isoforms in the sample is indicative of an acute bone fracture in the individual.

A further embodiment of the present invention is a method for diagnosing acute pancreatitis in an individual comprising: testing a blood sample from an individual to determine the presence in the sample of the BMP-1 isoform BMP-1-7, wherein the presence of said BMP-1 isoform in circulating blood of said individual is indicative of acute pancreatitis in the individual.

A further embodiment of the present invention is a method for diagnosing chronic renal failure in an individual comprising: testing a blood sample from an individual to determine the presence in the sample of the BMP-1 isoforms BMP-1-3 and BMP-1-5, wherein the presence of both said BMP-1 isoforms in circulating blood of said individual is indicative of chronic renal failure in said individual.

A particularly advantageous method disclosed herein is a method for diagnosing fibrodysplasia ossificans progressive in an individual comprising: testing a blood sample from an individual to determine the presence in the sample of the BMP-1 isoform BMP-1-3, wherein elevated levels (for example at least 5 times) of said BMP-1 isoform in comparison with levels of the same isoform in a healthy individual is indicative of fibrodysplasia ossificans progressive in said individual.

Another particularly advantageous embodiment of the present invention is a method for diagnosing osteogenesis imperfecta in an individual comprising: testing a blood sample from an individual to determine the presence in the sample of the BMP-1 isoform BMP-1-3, wherein elevated levels (for example, at least 5 times) of said BMP-1 isoform in comparison with levels of the same isoform in a healthy individual is indicative of osteogenesis imperfecta in said individual.

A further embodiment of the present invention is a method of treating an individual for a defect or disorder in bone or soft tissue of an individual comprising:
  (a) diagnosing a defect or disorder in a bone or soft tissue in an individual by steps comprising:
    (i) determining the profile of BMP-1 isoforms in the blood and
    (ii) comparing the profile to a standard blood profile of BMP-1 isoforms associated with various defects and disorders,
  (b) administering to the individual an amount of at least one BMP-1 isoform effective to enhance the therapeutic effect of an osteogenic BMP toward the diagnosed defect or disorder, or administering to the individual an amount of one or more antibody molecules specific for one or more BMP-1 isoforms effective to inhibit the effects of said one or more BMP-1 isoforms in the progression of the diagnosed defect or disorder.

The diagnosing step (a) of the foregoing method may be performed by comparing the patient's blood BMP-1 isoform profile with, for example, the standard blood isoform association table shown in Table 1, below. The therapeutic step (b) of the foregoing method may be accomplished via systemic or local administration of the therapeutic agent. In treating bone defects in particular, local administration to the area of the defect is preferred. Local administration of BMP-1 isoform BMP-1-1, for instance, is shown herein to accelerate bone repair in in vivo fracture models. (See, Examples 12 and 14, below.) Local administration of a BMP-1 isoform and/or an authentic, osteogenic BMP such as BMP-7 may advantageously be effected using a whole blood coagulum as a carrier/matrix for localized delivery of those agents to the bone defect. A whole blood-derived coagulum device is described herein which provides a mechanically stable (self-supporting) therapeutic with the consistency of a gel, which in turn is easily applied to bone ends or in a gap between bone sections where rebridgement of bone is desired.

In particular embodiments of the foregoing diagnostic methods, the detection step will be directed toward detecting one or more of BMP-1-1, BMP-1-3, BMP-1-5, and BMP-1-7, having the amino acid sequences shown in SEQ ID NO:1, SEQ ID NOS:2 or 4, SEQ ID NO:6, and SEQ ID NO:7, respectively, or detecting an epitope or a detectable fragment (such as a tryptic fragment) of said amino acid sequences.

In a particular embodiment, the present invention provides an osteogenic whole blood-derived coagulum device (WBCD) for treating a bone defect in an individual prepared by mixing together in an aliquot of whole blood a substance providing calcium ions ($Ca^{++}$), such as calcium chloride; at least one BMP-1 isoform and optionally at least one osteogenic BMP; and optionally a composition comprising fibrin and thrombin. The mixture is incubated until a coagulum having the consistency of a mechanically stable gel forms, and thereafter the coagulum is easily applied as a matrix to the site where bone rebridgement or repair is desired. Such mechanically stable gel will preferably be homogenous, cohesive, syringeable, injectable and malleable. The consistency of the coagulum ensures that the mixture, entraining the therapeutic BMP (if present) and BMP-1 isoform, will remain in place adjacent the bone defect to be repaired.

The proportions of the ingredients of the coagulum may be varied, but the amount of calcium ion substance should be such that the concentration of calcium ion provides a coagulum gel having the desired features mentioned above. A preferred concentration of calcium ions in the coagulum will fall in the range of 1-2.5 mM. Calcium chloride is a preferred exogenous $Ca^{++}$-supplying substance. When calcium chloride is used in a WBCD of the invention, the concentration is advantageously in the range of 5-15 mM.

The amount of BMP-1 isoform in a coagulum according to the invention is advantageously in the range of 1-500 µg/mL, preferably 2-200 µg/mL, more preferably 5-20 µg/mL, although lesser or greater amounts may also be used: it is a basic discovery disclosed herein that the presence of BMP-1 isoforms is helpful to catalyze the activity of authentic, osteogenic BMPs locally, e.g., in repairing bone defects and rebridging bone fractures. Thus, any amount of a BMP-1 isoform effective to enhance the osteogenic activity of BMP (whether activated from the extracellular matrix or supplied exogenously, e.g., as a component of a whole blood-derived coagulum device) may be used. Similarly, if one or more BMP is used as a component of a coagulum device according to the invention, the amount may advantageously be adjusted to fall in the range of 50-500 µg/mL, preferably 100-200 µg/mL. As with the BMP-1 isoform component, however, lesser or greater amounts are contemplated, and any amount of a BMP effective to promote osteogenesis at the intended site of the bone defect may be used. Alternatively, the amounts of a BMP-1 isoform or a BMP used in a coagulum may be adjusted to provide an overall dose of isoform or BMP based on the overall weight of the individual, considering the amount of coagulum to be used. For example, an amount of BMP-1 isoform to provide 2-200 µg/kg, preferably 5-20 µg/kg, more preferably 8-12 µg/kg patient weight, may be used; and an amount of a BMP to provide, e.g., 1-1000 µg/kg, preferably 2-500 µg/kg, more preferably 50-200 µg/kg, most preferably 100 µg/kg patient weight, may be used. In determining the amounts of ingredients for use in a WBCD, it will be understood that the amounts or volumes of the ingredients cannot be so much (or so little) as to adversely affect the desired features of the coagulum gel.

Accordingly, in a particular embodiment of the invention, an osteogenic whole blood-derived coagulum device (WBCD) for treating a bone defect in an individual is prepared by the steps comprising:
 (a) mixing together:
  (i) whole blood,
  (ii) 2-200 µg/mL of at least one BMP-1 isoform,
  (iii) 5-15 millimoles/L calcium chloride,
  (iv) optionally, a mixture comprising 5-10 mg/mL fibrin and 0.5-5 mg/mL thrombin; and
 (b) incubating the mixture of step (a) until a mechanically stable gel is formed.

If desired, an amount of a BMP, preferably in the range of 50-500 µg/mL, may be added to the mixture of (a) in the foregoing embodiment, to take advantage of the synergistic effect of the combination of BMP-1 isoform and BMP disclosed herein.

Many suitable substances for providing calcium ions are known. Calcium chloride is preferred.

Fibrin-thrombin mixtures useful in a WBCD described herein may be made by simply mixing fibrin and thrombin in with the other ingredients of the WBCD.

Alternatively, fibrin and thrombin may be premixed or purchased as a mixture and the mixture then added to the other ingredients. Fibrin-thrombin mixtures useful in a WBCD include those known in the art as "fibrin glue" or "fibrin sealant". Commercial preparations of fibrin-thrombin mixtures, fibrin glues, and fibrin sealants are readily available. Fibrin and thrombin used in preparing a WBCD as described herein are of pharmaceutically acceptable quality and are not a source of significant immunogenicity that would normally elicit an immune response in most individuals.

An exogenously provided fibrin-thrombin mixture may enhance one or more of the properties provided to the coagulum gel by calcium ion as mentioned above. In addition, a fibrin-thrombin mixture can also be used to entrap the BMP-1 isoform (and optional BMP) component(s) of a WBCD. Such entrapment of such active ingredients enhances retention by the WBCD and thereby decreases the rate of migration of the active ingredients from the WBCD and the local defect site to which the WBCD has been applied. Preferably, the exogenously provided fibrin-thrombin mixture used in a WBCD described herein provides fibrin in the range of 5 mg/mL to 10 mg/mL, inclusive, and provides thrombin in the range of 0.5 mg/mL to 5 mg/mL.

In preparing the osteogenic UVBCD according to the invention, the whole blood is most preferably autologous whole blood drawn from the individual. Thus, it is contemplated that the WBCD will be prepared for use in bone repair surgery, in the operating theater, immediately prior to use, and employing the patient's own whole blood to make the WBCD. This has the obvious advantage of avoiding the necessity of typing and cross-matching donor blood for administration to a particular patient. Nevertheless, it is recognized that in some situations, crossmatched whole blood may be used as, e.g., when a patient may already have lost a significant amount of blood or may already be receiving a blood transfusion. In such situations, the use of crossmatched whole blood in a WBCD introduces the same or similar risks of serum sickness associated with any transfusion employing crossmatched whole blood.

In a particular embodiment, the osteogenic WBCD according to the invention may be prepared by first combining any fibrin/thrombin composition, the calcium ion substance, and the BMP-1 isoform and optionally BMP to form a first mixture, then adding whole blood to the first mixture to form a second mixture, and incubating the second mixture until a mechanically stable (self-supporting) gel is formed.

In another embodiment, all the components necessary for preparation of a WBCD except the whole blood component may be conveniently and advantageously collected in a kit. The kit may be opened and used in the operating room at the moment it is needed, to form a WBCD using autologous blood obtained from the patient. Such a kit could include, for example, the following items:
(a) a vial containing one or more lyophilized BMP-1 isoform,
(b) a buffer for reconstituting the lyophilized BMP-1 isoforms(s),
(c) a syringe for reconstituting the lyophilized BMP-1 isoform(s) in the buffer,
(d) a vaccutainer for collecting a patient's blood,
(e) a sterile solution of 1 M calcium chloride,
(f) a fibrin-thrombin mixture,
(g) a container for mixing whole blood with the reconstituted BMP-1 isoform(s) and other ingredients,
(h) a spatula or syringe (or both) suitable for applying an osteogenic coagulum to bone ends during open bone repair surgery, and
(i) instructions for the preparation and use of a WBCD comprised of whole blood mixed with one or more BMP-1 isoforms, calcium chloride and, optionally, a mixture comprising fibrin and thrombin, to form a mechanically stable gel suitable for application to a bone defect.

The discoveries disclosed herein provide new approaches to therapy of bone defects and soft tissue disorders, based on the discovered role of BMP-1 isoforms and their presence in circulating blood.

In a particular embodiment, a method is provided for treating ischemic acute renal failure in an individual comprising administering a BMP-1 isoform systemically to the individual after diagnosis of renal injury. (See, Example 8, below.) In a related embodiment, a method is provided for treating chronic renal failure in an individual comprising administering systemically to the individual one or more antibody molecules specific for one or more BMP-1 isoforms. (See, Example 9, below.) In a particular embodiment of this method, the antibody molecule is an antibody molecule specific for the BMP-1-1 isoform, an antibody molecule specific for the BMP-1-3 isoform, or a combination of such antibody molecules.

A further embodiment of the invention provides a method of treating ischemia/reperfusion damage to a kidney in an individual comprising: administering to the individual one or more antibody molecules specific for one or more BMP-1 isoforms in an amount effective to inhibit ischemia/reperfusion injury in said individual. In particular embodiments, one or more antibody molecules recognizing one or more BMP-1 isoforms is administered systemically to the individual prior to an ischemia/reperfusion event. In particular, an antibody molecule binding to BMP-1-1, an antibody molecule binding to BMP-1-3, or a combination of such antibody molecules may be administered to the individual.

The present invention also provides a method of pretreating an individual to resolve clots that may occur during thoracic or abdominal surgery comprising administering a BMP-1 isoform to the individual prior to surgery in an amount effective to resolve clots that occur.

A further embodiment of the present invention provides a method of treating acute pancreatitis in an individual comprising administering to the individual a therapeutically effective amount of at least one antibody molecule specific for a BMP-1 isoform. In particular, in this embodiment, an anti-BMP-1-7 antibody molecule may be used.

A further embodiment of the present invention provides a method of treating pancreatitis in an individual comprising administering to an individual suffering from pancreatitis, after the acute phase of the inflammatory process, an amount of a BMP-1 isoform in an amount effective to promote pancreatic regeneration. In particular, in this embodiment, the BMP-1-7 isoform may be administered.

In the course of our investigation of circulating BMP-1 isoforms, we also isolated, from a placental cDNA library, a polynucleotide encoding a previously unreported variant of BMP-1 isoform BMP-1-3. The coding sequence for this isoform is shown in SEQ ID NO:5; the amino acid sequence for this variant isoform is shown in SEQ ID NO:4. The BMP-1-3 isoform expressed from the isolated placental cDNA exhibits some additional properties as compared to the previously reported BMP-1-3 isoform (SEQ ID NO:2). (See, Example 5, below.) Accordingly, an additional aspect of the present invention is to provide an isolated polynucleotide encoding the polypeptide having the amino acid sequence of SEQ ID NO:4. One such polynucleotide has the sequence of SEQ ID NO:5.

In its broadest aspects, the present invention relates to the use of a detector molecule that specifically binds a BMP-1 isoform in an in vitro diagnostic method to test for the presence of one or more BMP-1 isoforms in circulating blood of an individual, for diagnosing a defect or disorder in bone or soft tissue in said individual. In preferred embodiments such a detector molecule is an antibody molecule or an aptamer. Advantageously, such detector molecules are detectably labeled.

The present invention, in its therapeutic aspects, provides for the use of a BMP-1 isoform in the manufacture of a medicament for the treatment of bone defects. Also, the present invention provides for the use of an antibody molecule that binds a BMP-1 isoform in the manufacture of a medicament for treatment of soft tissue disorders as herein described.

BRIEF DESCRIPTION OF THE DRAWINGS

FIG. 2 shows histological sections of kidney tissues from rats subjected to ischemia/reperfusion acute renal failure as described for FIG. 1, above, and in Example 7, below. Panel 2A shows a representative histological section of kidney tissue from a rat of the control group that was subjected to acute ischemia/reperfusion injury without antibody therapy (physiological saline vehicle, pH 7.2, only). Significant loss of structural integrity of kidney tissue is evident in Panel 2A. Panel 2B shows a representative histological section of kidney tissue from a rat of the prophylactic therapy group that was systemically administered antibodies to BMP-1-1 and BMP-1-3 prior to acute ischemia/reperfusion injury and for five days thereafter. Tissue in Panel 2B indicates significant preservation of kidney structures, as compared to the untreated tissues depicted in Panel 2A. See, Example 7, below, for details.

FIG. 4 shows fractures in femurs after 8 weeks from rats treated systemically with BMP-1-1 (bones 4A and 4D), BMP-7 (bones 4B, 4C, and 4E), and antibody to BMP-1-1 (bone 4F). Systemic administration of BMP-1-1 to rats resulted in accelerated healing of fractures as compared to systemic administration of BMP-7 to rats. Systemic administration of BMP-1-1 neutralizing antibody delayed the fracture healing due inhibition of BMP-1-1 activity at the fracture site.

FIGS. 7A and 7B show ulnar defect in representative bone after 6 weeks from rabbits treated locally with a WBCD containing BMP-7 as described in Example 14, below.

FIGS. 8A and 8B show ulnar defect in representative bone after 6 weeks from rabbits treated locally with a WBCD containing BMP-1-1 and BMP-7 as described in Example 14, below.

DETAILED DESCRIPTION OF THE INVENTION

Figure 1:
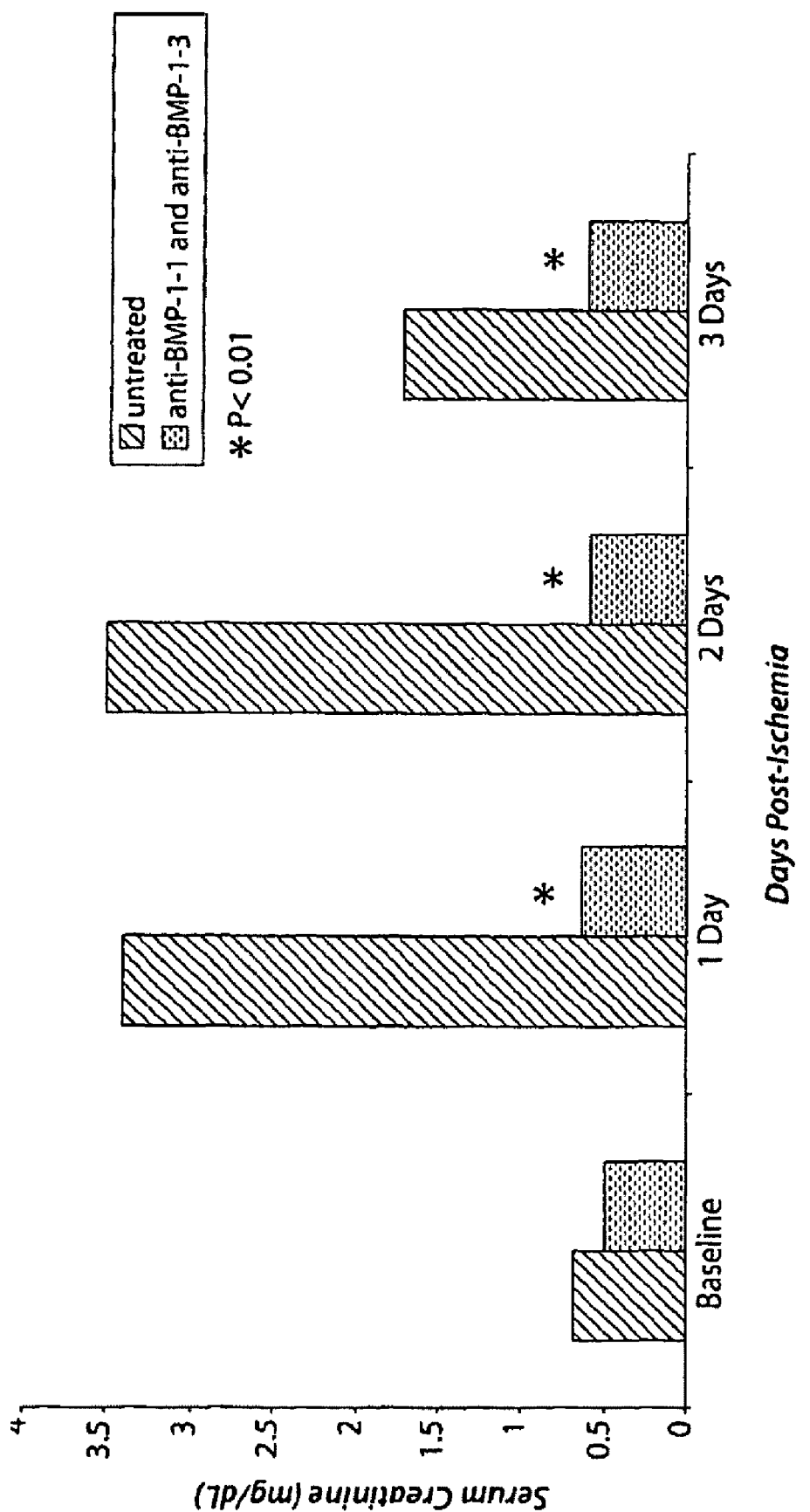
FIG. 1 shows a graph of the concentration (mg/dL) of creatinine versus time (days) in blood of rats subjected to ischemic acute renal failure. Diagonal line bars show levels of creatinine in the blood of rats of the control group (ischemia, no treatment) at indicated times after the ischemic event. Stippled bars show levels of creatinine in blood of rats treated systemically with antibodies to BMP-1-1 and to BMP-1-3 prior to ischemia and for five days thereafter. Asterisks indicate significant (P<0.01) difference between creatinine levels between animals treated with antibodies and those of the untreated control group. The results indicate that systemic administration of BMP-1-1 and BMP-1-3 neutralizing antibodies prevented loss of kidney function in rats with ischemia/reperfusion acute renal failure if administered prior to injury. See Example 7, below, for details.

In order that the invention may be fully understood the following terms are defined.

"Antibody" or "antibody molecule", as used and understood herein, refers to a specific binding member that is a protein molecule or portion thereof or any other molecule, whether produced naturally, synthetically, or semi-synthetically, which possesses an antigenic binding domain formed by an immunoglobulin variable light chain region or domain ($V_L$) or portion thereof, an immunoglobulin variable heavy chain region or domain ($V_H$) or portion thereof, or a combination thereof. The term "antibody" also covers any polypeptide or protein molecule that has an antigen-binding domain that is identical, or homologous to, an antigen-binding domain of an immunoglobulin. Antibodies may be "polyclonal", i.e., a population of antigen-binding molecules that bind to different sites on the antigen, or "monoclonal", i.e., a population of identical antigen-binding molecules that bind to only one site on an antigen. Examples of an antibody molecule, as used and understood herein, include any of the well known classes of immunoglobulins (e.g., IgG, IgM, IgA, IgE, IgD) and their isotypes; fragments of immunoglobulins that comprise an antigen binding domain, such as Fab or F(ab')$_2$ molecules; single chain antibody (scFv) molecules; double scFv molecules; single domain antibody (dAb) molecules; Fd molecules; diabody molecules; and fusion proteins comprising such molecules. Diabodies are formed by association of two diabody monomers, which form a dimer that contains two complete antigen binding domains wherein each binding domain is itself formed by the intermolecular association of a region from each of the two monomers (see, e.g., Holliger et al., *Proc. Natl. Acad. Sci. USA,* 90: 6444-6448 (1993)). Use of such antibody molecules offers the vast array of antibody detection systems and formats available in the art that may be adapted to selectively detect particular BMP-1 isoforms in mixtures, including whole blood, plasma, serum, and various tissue extracts. Examples of formats for using antibody molecules to detect BMP-1 isoforms may include, but are not limited to, immunoblotting (e.g., Western blots, dot blots), immunoprecipitations, affinity methods, immunochips, and the like. Any of a variety methods known in the art may be employed to produce antibody molecules to a specific BMP-1 isoform or a portion thereof comprising at least one epitope (antibody binding site) of the BMP-1 isoform.

"Circulate" and "circulating" describe anything that travels or is otherwise transported through the vascular system of an individual.

The terms "disorder" and "disease" are synonymous and refer to any pathological condition, irrespective of cause or etiological agent. A "defect" in a tissue refers to a site of abnormal or deficient tissue growth. A "disease" or "disorder" may be characterized by one or more "defects" in one or more tissues.

As used herein, the terms "treatment" and "treating" refer to any regimen that alleviates one or more symptoms or manifestations of a disease or disorder, that inhibits progression of a disease or disorder, that arrests progression or reverses progression (causes regression) of a disease or disorder, or that prevents onset of a disease or disorder. Treatment includes prophylaxis and includes but does not require cure of a disease or disorder.

A "therapeutically effective amount" is an amount of a compound (e.g., a BMP-1 isoform or a BMP-1 isoform binding molecule when used therapeutically) which inhibits, totally or partially, the progression of the condition, which alleviates, at least partially, one or more symptoms of the disorder, or which enhances or catalyzes the therapeutic or otherwise beneficial effects of another compound (e.g., an osteogenic BMP). A therapeutically effective amount can also be an amount which is prophylactically effective. The amount which is therapeutically effective will depend upon the patient's size and gender, the condition to be treated, the severity of the condition and the result sought. For a given patient, a therapeutically effective amount can be determined by methods known to those of skill in the art.

The term "isolated" when used to describe the various polypeptides disclosed herein, means a polypeptide that has been identified and separated and/or recovered from a component of its natural environment. Contaminant components of its natural environment are materials that would typically interfere with diagnostic or therapeutic uses for the polypeptide, and may include enzymes, hormones, and other proteinaceous or non-proteinaceous solutes. Isolated polypeptide includes polypeptide in situ within recombinant cells engineered to express it, since at least one component of the polypeptide's natural environment will not be present. Ordinarily, however, isolated polypeptide will be prepared by at least one purification step. An "isolated polynucleotide" or isolated polypeptide-encoding nucleic acid is a nucleic acid molecule that is identified and separated from at least one contaminant nucleic acid molecule with which it is ordinarily associated in the natural source of such nucleic acid, e.g., the human genome. An isolated polynucleotide is other than in the form or setting in which it is found in nature. Isolated polynucleotides therefore are distinguished from the specific polypeptide-encoding nucleic acid molecule as it exists in natural cells. However, an isolated polynucleotide includes polypeptide-encoding nucleic acid molecules contained in cells that ordinarily express the polypeptide but where, for example, the nucleic acid molecule is in a chromosomal location different from that of natural cells.

"Gel" means a semi-solid jelly-like material.

"Homogenous", as applied to a coagulum gel, means that the coagulum gel has a uniform consistency as opposed to a nonuniform fibrous network connecting clumps of clots.

"Syringeable" as used herein to describe a coagulum gel means that the coagulum gel can be drawn up into a syringe with a needle in the range of 18 to 23 gauge, inclusive, without clogging the needle or breaking up into clumps.

"Injectable" as used herein to describe a coagulum gel means that the coagulum gel can be expelled from a syringe through the aperture of the syringe or through a needle in the range of 18 to 23 gauge, inclusive, without clogging the aperture or needle and without breaking up into clumps.

"Malleable" as used herein to describe a coagulum gel means that the coagulum gel is capable of being shaped or formed to fill or cover a bone defect. A malleable coagulum gel is self-supporting (or mechanically stable) and will substantially retain the shape into which it was formed.

A composition or method described herein as "comprising" one or more named elements or steps is open-ended, meaning that the named elements or steps are essential, but other elements or steps may be added within the scope of the composition or method. To avoid prolixity, it is also understood that any composition or method described herein as "comprising" (or "which comprises") one or more named elements or steps also describes the corresponding, more limited, composition or method "consisting essentially of" (or "which consists essentially of") the same named elements or steps, meaning that the composition or method includes the named essential elements or steps and may also include additional elements or steps that do not materially affect the basic and novel characteristic(s) of the composition or method. It is also understood that any composition or method described herein as "comprising" or "consisting essentially of" one or more named elements or steps also describes the corresponding, more limited, and close-ended composition or method "consisting of" (or "which consists of") the named elements or steps to the exclusion of any other unnamed element or step. In any composition or method disclosed herein, known or disclosed equivalents of any named essential element or step may be substituted for that element or step.

Unless indicated otherwise, the meaning of other terms is the same as understood and used by persons in the art, including the fields of medicine, biochemistry, molecular biology, and tissue regeneration.

The invention is based on the discovery that BMP-1 isoforms in the blood of an adult individual (human or other mammal) are useful as biological markers (biomarkers) for the state or condition of the tissues of the individual. In particular, the presence or absence of one or more isoforms of BMP-1 in the blood, i.e., the BMP-1 isoform blood profile, of an adult individual is indicative of the health or a particular pathological state of bone and various soft tissues of the individual. BMP-1-1, which is identical to the metalloproteinase procollagen C-proteinase (also referred to as BMP-1 procollagen C-proteinase) was originally discovered in the bone matrix. However, the BMP-1-1 isoform is not found circulating in the blood of the healthy adult individual, nor in patients with various diseases. Previously, the existence of isoforms other than BMP-1-1 was inferred only at the level of tissue RNA transcripts.

Table 1, below, provides profiles of circulating BMP-1 isoforms associated with normal health and with several disorders, i.e., an acute bone fracture, chronic renal failure, fibrodysplasia ossificans progressive (FOP), osteogenesis imperfecta (IO), acute pancreatitis, and cirrhosis of the liver. A description of the study that generated the diagnostic profiles in Table 1 is provided in Example 6 (below).

TABLE 1

BMP-1 isoforms in various tissue defects and disorders

| | BMP Isoform | | | |
|---|---|---|---|---|
| Pathology of Patient | BMP-1-1 | BMP-1-3 | BMP-1-5 | BMP-1-7 |
| healthy (normal) | – | + | – | – |
| acute bone fracture | – | – | – | – |
| chronic renal failure | – | + | + | – |
| FOP | – | ++ | – | – |
| OI | – | ++ | – | – |
| acute pancreatitis | – | – | – | + |
| liver cirrhosis | – | – | – | – |

FOP = fibrodysplasia ossificans progressive; IO = osteogenesis imperfecta
++ indicates much higher than normal levels (i.e., at least 5-fold higher than in healthy individuals)

Blood obtained from an individual can be easily analyzed for the presence of various BMP-1 isoforms, e.g., using isoform-specific antibodies or other isoform detector molecules. The profile of BMP-1 isoforms in the blood sample can then be compared to the profiles in Table 1 to diagnose any of the indicated pathological states.

Table 1 shows that circulating BMP-1 isoforms are useful as biological markers (i.e., biomarkers) of a broad, spectrum of diseases. The use of the BMP-1 isoform blood profiles to diagnose the pathologies in Table 1 is not dependent on an understanding of the mechanism by which such profiles are generated. Nevertheless, there are implications to the data presented herein beyond providing a convenient method of diagnosing various disorders. In particular, data presented herein demonstrate for the first time the existence of circulating enzymes that are variant products of a single gene, BMP-1. Moreover, without wishing to be bound by any particular mechanism or theory of operation, the data in Table 1 dispel a long-held model for the action of authentic osteogenic BMPs in which each tissue or organ was assumed to release a particular authentic BMP (e.g., BMP-4, BMP-5, BMP-6) into the circulation during injury and in the process of regeneration of that tissue or organ. On the contrary, as shown in Table 1, in healthy individuals only the BMP-1-3 isoform circulates, and no authentic osteogenic BMPs have been found in the blood of healthy individuals (see, Example 1, below). Moreover, as shown herein, as much as 80% of intravenously administered BMP-1-3 becomes localized at the orthotopic site of fractured femurs in rats and results in an accelerated rate of bone healing compared to untreated control animals (see, Example 7, below). In addition, in cultures of rat calvariae, which are rich in ECM, exogenously provided BMP-1-3 promotes release into the culture medium of authentic osteogenic BMP-4 and BMP-7 (see, Example 9, below). These data are more consistent with the tissue repair model shown herein, that circulating BMP-1 isoforms can act catalytically as key processing enzymes of the ECM (which is a repository of authentic osteogenic BMP molecules (see, e.g., Martinovic et al., *Arch. Cytol. Histol.,* 1: 23-36 (2006))) to effect a local release of one or more authentic osteogenic BMPs. In bone repair, for example, BMP-1 isoform-catalyzed release of authentic BMP locally acts in turn locally to promote bone regeneration and repair during the formation of callus during the rebridgement of fractured bone ends.

As shown in Table 1, a number of pathological conditions are characterized by a disappearance of the BMP-1-3 isoform from the blood, i.e., acute bone fracture, acute pancreatitis, and liver cirrhosis. If in addition to BMP-1-3, the BMP-1-5 isoform is also present in the blood of an individual, then the isoform profile is diagnostic of chronic renal failure (CRF). If BMP-1-3 is found in the blood at much higher concentrations than in a normal individual (i.e., at least 5 times the normal level), then the isoform profile is diagnostic of FOP or OI. If BMP-1-7 is the only isoform present, then the profile is diagnostic of acute pancreatitis.

With respect to soft tissue organs, an absence of BMP-1-3 in the blood may indicate a condition in which the BMP-1-3 accumulates in a parenchymal organ to facilitate processing of the extracellular matrix (ECM), which in turn stimulates fibrosis. A common feature of the soft tissue pathologies in Table 1 is a progressing fibrosis of the tissue, which untreated can lead to organ failure. Such fibrosis is characteristic of cirrhosis of the liver and acute pancreatitis. Accordingly, when a blood profile indicates the absence of BMP-1-3, and there is no evidence of bone fracture, chronic renal failure, FOP, or OI, then Table 1 directs the diagnosis to the specified pathologies of parenchyma organs, such as liver or pancreas. In such situations, the healthcare professional is alerted to perform additional tests for pathology in such organs. Accordingly, such additional tests may include determining whether one or more parenchyma organs exhibits increased fibrosis as evidenced by performing standard tests for an accumulation of collagen, laminin, fibronectin, and other extracellular molecules leading to increased fibrosis.

For Table 1, the sera from patients with acute pancreatitis were collected at an early stage of the disease, i.e., prior to robust serum elevation of the pancreatic enzymes such as pancreatic amylase and lipase. Surprisingly, the blood of these patients contained the BMP-1-7 isoform, which has not been previously detected at the protein level (that is, as an expressed protein rather than a theoretical BMP variant deduced from detection of mRNA transcripts). The appearance in the blood of BMP-1-7 is useful as an early diagnostic marker for acute injury of the pancreas.

The BMP-1-3 and BMP-1-5 isoforms were found in patients with chronic kidney failure on dialysis and suggest a specific function of these isoforms in the disorder, e.g., involvement in the fibrotic processes in bone called renal osteodystrophy. The BMP-1-5 isoform has also been detected in the circulation of rats with chronic renal failure reflecting the severity of the disease. Our detection of BMP-1-5 in the blood of patients is also the first demonstration of the BMP-1-5 isoform on the protein level.

According to the profiles in Table 1, a BMP-1 isoform profile that indicates there are no BMP-1 isoforms circulating in the blood of a patient is evidence that the individual has an acute bone fracture and/or has liver cirrhosis. Both of these conditions involve fibrosis. Such fibrosis may be beneficial as part of callus formation in the healing of an acute bone fraction, whereas in soft tissue, fibrosis is destructive and is characteristic of liver cirrhosis.

Determining the circulating BMP-1 isoform profile may be used not only when an individual presents symptoms of a tissue defect or disease, but also as part of an individual's routine blood test conducted by an attending healthcare professional, e.g., as part of an annual physical examination. BMP-1 isoforms are readily detected in samples of blood obtained from an individual using any of a variety of methods and compositions known in the art. Such methods include, but are not limited to, high performance liquid chromatography (HPLC), mass spectrometry (MS) of tryptic peptides of BMP-1 isoforms, and affinity methods, particularly those that employ affinity molecules that specifically bind a particular BMP-1 isoform to the exclusion of other isoforms. Such affinity molecules include, but are not limited to, antibody molecules and aptamers. Antibody molecules specific for each BMP-1 isoform are particularly preferred as there is a wide variety of assay formats available in the art that can employ an antibody molecule to detect or isolate a target protein present in the blood of an individual. Such formats include, but are not limited to, filter paper (e.g., nitrocellulose, cellulose acetate), microtiter plates, polymeric particles (e.g., agarose, polyacrylamide), silicon chips, etc. It is understood that for any particular method used to detect or isolate a BMP-1 isoform from the blood of an individual, it may be preferred to make such detection or isolation from the plasma or serum portion of whole blood.

Recombinant BMP-1 isoforms described herein were cloned and expressed in eukaryotic and prokaryotic host cells. Such recombinant cells may be employed to produce sufficient amounts of the isoforms for use in the methods described herein. The specific coding sequences for each of the BMP-1 isoforms discussed herein is known, and the encoded amino acid sequences have been deduced. See, e.g., EMBL Nucleotide Sequence Database (worldwide web.ebi-.ac.uk/embl). For convenience, the amino acid sequence for BMP-1-1 is included herein as SEQ ID NO:1. The amino acid sequence for BPM-1 isoform BMP-1-3 is shown in SEQ ID NO:2, and a cDNA sequence coding for BMP-1-3 is shown in SEQ ID NO:3. The amino acid sequence for BMP-1 isoform BMP-1-5 is shown in SEQ ID NO:6. The amino acid sequence for BMP-1 isoform BMP-1-7 is shown in SEQ ID NO:7. A new variant form of BMP-1-3 derived from human placenta and having properties that differ from the previously known form of BMP-1-3 has been discovered, having the amino acid sequence of SEQ ID NO:4 and a coding sequence shown in SEQ ID NO:5.

BMP-1 isoforms and peptides thereof may be produced by standard recombinant, synthetic, or semi-synthetic methods available in the art. BMP-1 isoforms and peptides thereof may also be used to produce various affinity molecules, including polyclonal and monoclonal antibody molecules, using standard methods available in the art.

All or a portion of a nucleotide sequence encoding the isoforms of SEQ ID NOS:1, 2, 4, 6, and 7 may be incorporated into the nucleotide sequence of any of a variety of nucleic acid molecules, such as vectors, primers, nucleic acid probes for hybridization, and the like. Such recombinant nucleic acid molecules may be used to clone nucleic acid molecules encoding a BMP-1 isoform of interest, to identify or detect BMP-1 isoform nucleotide sequences (e.g., by various hybridization methods), and/or to amplify a nucleic acid molecule encoding a BMP-1 isoform of interest (e.g., using a polymerase chain reaction (PCR) protocol). Nucleic acid molecules may be synthesized chemically (e.g., using an automated nucleic acid synthesizer), produced by PCR, and/or produced by various recombinant nucleic acid methods known in the art. Nucleic acid molecules may be synthesized with various modifications known in the art to provide molecules that resist cleavage by various nucleases and chemicals, such as replacing phosphodiester linkages with thiol linkages. Methods of detecting a specific nucleotide sequence (DNA, cDNA, or RNA) encoding all or a portion of a BMP-1 isoform are well known in the art and include, without limitation, Southern blots (for DNA and cDNA), Northern blots (for RNA), polymerase chain reaction (PCR) methods, dot blots, colony blots, and in vitro transcription of DNA or cDNA molecules. Nucleic acid molecules as described herein may also be immobilized by standard methods to any of a variety surfaces including but not limited to a cellulose-containing paper (e.g., nitrocellulose, cellulose acetate), nylon, a well of a plastic microtiter dish, polymeric particles (e.g., agarose particle, acrylamide particles), and a silicon chip.

The profiles in Table 1 also suggest possible targets for drug discovery and new methods of treating defects and disorders. For example, as noted above, BMP-1 isoforms are implicated as key enzymes to promote fibrosis. Accordingly, fibrotic diseases may be treated by inhibiting or inactivating one or more BMP-1 isoforms that are implicated in tissue fibrosis. A preferred method of treating a fibrotic disease comprises administering to a patient an antibody to a BMP-1 isoform associated with tissue fibrosis. Such fibrotic diseases include, without limitation, fibrotic kidney disease, liver cirrhosis, acute pancreatitis, and FOP. For example, in a method of treating a patient with chronic renal failure and on dialysis therapy, an antibody to a BMP-1 isoform(s) may be administered to the patient to delay the kidney failure and prevent the development of renal osteodystrophy, which leads to fragile bones and fibrotic bone marrow that inhibits the regenerative process. In patients with FOP, an antibody molecule may be administered to inhibit a BMP-1 isoform to prevent or inhibit ectopic ossifications, which depend on the fibrotic process to develop the characteristic "second skeleton" of FOP patients. Preferably, an antibody molecule useful in methods described herein is an antibody molecule that has very low or, most preferably, no immunogenicity, so that the antibody molecule may be administered in multiple doses to a patient without invoking an immune response in the patient that would inactivate the antibody molecule. It is also understood that administration of a therapeutic agent, such as an antibody, to inhibit or inactivate a BMP-1 isoform, may also inhibit healing of bone fractures, which depends on fibrosis in the formation of a bone callus in normal healing of fractures. Accordingly, it will be appreciated by the healthcare professional that a therapy described herein to inhibit a BMP-1 isoform(s) is not recommended until any bone fractures that may be present in a patient have healed or unless the healing of any fractures in the patient is outweighed by a more critical need for therapy to inhibit or inactivate a BMP-1 isoform(s).

Another method of treatment of the invention comprises administering a recombinant BMP-1 isoform to a patient lacking a particular BMP-1 isoform that could accelerate tissue repair or that could prevent a disease. As shown herein, BMP-1-3 disappears from circulation and becomes localized in the orthotopic site of acute bone fracture.

Administration of recombinant BMP-1-1 to an individual that has sustained an acute form of a disease can accelerate bone repair whether the BMP-1 isoform is administered systemically (see, Example 7, below) or locally (see, Example 8, below). Administration of a BMP-1 isoform may also be employed therapeutically to resolve blood clots that can occur in patients following an ischemic acute renal failure during major open surgery, such as thoracic or abdominal surgery. In such cases, a BMP-1 isoform is preferably administered prior to surgery as a preventative therapy for resolving clots that might form during the surgery.

In patients with acute pancreatitis, inhibition of the BMP-1-7 isoform may be used prophylactically to prevent or to inhibit progression of the disease, while systemic administration of BMP-1-7 following the acute phase of the inflammatory process may be used to promote pancreatic regeneration. The dual function of BMP-1 isoforms was shown in acute renal failure in rats, where BMP-1-1 and BMP-1-3 antibodies injected prior to kidney ischemia preserved the kidney function, while systemic administration of BMP-1-1 isoform following the ischemia resulted in a significantly greater survival of rats (see, Example 11, below). Thus, a dual function of BMP-1-1 isoform in an acute ischemic disease suggests two treatment methods, i.e., a preventative (prophylactic) treatment and a therapeutic (regenerative) treatment. Accordingly, a method of preventing acute kidney ischemic disease may comprise administering (e.g., parenterally) to an individual an antibody to one or more BMP-1 isoforms, e.g., antibody to circulating BMP-1-3 isoform and an antibody to circulating BMP-1-1 isoform, to prevent fibrosis or to prevent substantial progression of fibrosis. In contrast, a method of treating acute ischemic kidney disease may comprise administering (e.g., parenterally) to an individual one or more recombinant BMP-1 isoforms to support better regeneration of the kidney(s) in a subacute stage of the disease. A method of treating chronic renal failure may comprise administering (e.g., parenterally) to an individual an antibody to one or more BMP-1 isoforms (e.g., antibody molecules to BMP-1-1 and to BMP-1-3) to inhibit fibrosis and progression of the disease. A healthcare professional is able to assess the condition of an individual's kidneys to determine whether the individual is at risk of acute ischemia and, therefore, is a candidate for preventative treatment (e.g., antibody molecules to inhibit BMP-1-3 and BMP-1-1 isoforms), or whether the individual already suffers from significant acute ischemic kidney disease, so as to be a candidate for the therapeutic (regenerative) treatment (administration of BMP-1 isoform(s)).

An important aspect of the findings described herein (see, Examples, below) is that contrary to the teachings and assumptions of the prior art, an osteogenic BMP of the BMP family (e.g., BMP-2, BMP-4, BMP-6, BMP-7, and the like) should not be administered systemically to provide therapeutic treatment for local repair of bone fractures or disorders since any compromise in the wall of a blood vessel may release the osteogenic BMP locally thereby potentially inducing ossification of local soft tissue. Such compromise of blood vessels readily occurs at injection sites, bruises, and wounds where the combination of locally available stem cells and an osteogenic BMP can result in undesired ossification of soft tissue (e.g., muscle tissue). In contrast, BMP-1 isoforms such as BMP-1-3 or BMP-1-1 may be administered systemically to release an osteogenic BMP from extracellular matrix at a local site of bone fracture. BMP-1-1 and its isoforms are not authentic BMPs but are enzymes.

A BMP-1 isoform may be employed as an active ingredient in a whole blood-derived coagulum device (WBCD) to treat a bone defect, such as a fracture or a bone that is characterized by inadequate bone growth (e.g., as occurs in various metabolic bone disorders), in an individual. Such WBCDs comprising one or more BMP-1 isoforms (e.g., BMP-1-1, BMP-1-3) may be implanted or injected into a site of fracture or other defect characterized by inadequate bone growth to promote bone regeneration. WBCDs prepared for the delivery of one or more BMPs are described in detail in commonly assigned, copending international application no. PCT/US07/016,601, filed 23 Jul. 2007 (Publication No. WO 2008/011192). The disclosure of that application is hereby incorporated by reference. The discovery as part of this invention that BMP-1 isoforms catalyze authentic, osteogenic BMPs from EMC (or introduced from exogenous sources) to enhance bone repair activity provides a basis for describing herein improved WBCDs which include at least one BMP-1 isoform or a combination of at least one BMP-1 isoform with at least one osteogenic BMP.

Thus, in a preferred embodiment, this invention provides an osteogenic WBCD for treating a bone fracture or other bone defect that is characterized by inadequate bone growth in an individual comprising:
 (a) whole blood;
 (b) a BMP-1 isoform in the amount of 1-500 µg/mL, preferably 2-200 µg/mL, more preferably 5-20 µg/mL, and optionally an authentic BMP in the amount of 50-500 µg/mL;
 (c) an exogenous substance to supply calcium ions ($Ca^{++}$) at a concentration of 1-2.5 mM; and
 (d) optionally, a mixture of 5-10 mg/mL fibrin and 0.5-5 mg/mL thrombin.

A whole blood-derived coagulum device described herein is preferably prepared by the steps comprising:
 (a) mixing together:
  (1) whole blood,
  (2) 1-500 µg/mL, preferably 2-200 µg/mL, more preferably 5-20 µg/mL, of at least one BMP-1 isoform,
  (3) 5-15 millimoles/L calcium chloride, and
  (4) optionally, a mixture of 5-10 mg/mL fibrin and 0.5-5 mg/mL thrombin;
 (b) incubating the mixture of step (a) until a mechanically stable (i.e., a non-fluid, self-supporting, adherent) coagulum gel is formed.

In the foregoing embodiment, one or more authentic, osteogenic BMPs, preferably in an amount of 50-500 µg/mL, may also be added to the mixing step (a).

In a preferred embodiment, the coagulum device is prepared by first combining the fibrin-thrombin mixture, calcium ion, and BMP-1 isoform or BMP components to form a first mixture; followed by combining said first mixture with whole blood until the concentrations of the ingredients fall within the ranges set forth above and a mechanically stable coagulum of gel consistency is formed.

Preferably, the whole blood used in the preparation of a WBCD described herein is the autologous whole blood drawn from the individual who is to receive the WBCD, as autologous whole blood will not be immunogenic, that is, will not be rejected as non-self tissue by the immune system of the recipient. Nevertheless, it is recognized that in some situations, crossmatched whole blood may be used as, e.g., when a patient may already have lost a significant amount of blood or may already be receiving a blood transfusion. In such situations, the use of crossmatched whole blood in the WBCD introduces the same or similar risks of serum sickness associated with any transfusion employing crossmatched whole blood.

The invention also provides kits for preparing an osteogenic whole blood-derived coagulum device (WBCD) containing one or more BMP-1 isoforms for treating a bone defect. For example, in a preferred embodiment, such a kit may be comprised of:
 (a) a vial containing lyophilized BMP-1 isoform(s),
 (b) a buffer for reconstituting the lyophilized BMP-1 isoforms(s) powder,
 (c) a syringe and a needle for reconstituting the lyophilized BMP-1 isoform(s) in the buffer,
 (d) a vaccutainer for collecting a patient's blood,
 (e) a sterile solution of 1 M calcium chloride,
 (f) a fibrin-thrombin mixture,
 (g) a container for mixing whole blood with the reconstituted BMP-1 isoform(s) and other ingredients,
 (h) a spatula or syringe (with or without a needle) (or both) for applying an osteogenic coagulum to bone ends during open bone repair surgery, and
 (i) instructions for the preparation and use of the WBCD containing BMP-1 isoform(s) using autologous or crossmatched whole blood.

EXAMPLES

Example 1

Purification of BMP-1 isoform, but not authentic osteogenic BMPs, from human blood plasma by heparin Sepharose affinity chromatography, and protein identification using liquid chromatography-mass spectrometry (LC-MS).

This study was originally made to determine whether any osteogenic BMPs could be detected and isolated from human blood plasma.

Plasma Collection

Blood samples from 50 healthy adult humans (21-50 years of age) were drawn into syringes containing 3.8% sodium citrate to form an anticoagulant-to-blood ratio (v/v) of 1:9. Plasma was obtained by centrifugation (15 min. at 3000×g), and aliquots of each adult blood sample were used to make a pooled plasma stock. Aliquot samples were stored at −80° C. prior to analysis.

Affinity Column Purification

Pooled human plasma (80 ml) was diluted 2-fold with 10 mM sodium phosphate buffer (pH 7), and applied to a 5 ml heparin Sepharose column (Amersham Pharmacia Biotech) previously equilibrated with 10 mM sodium phosphate buffer (pH 7). Bound proteins were eluted from the column with 10 mM sodium phosphate buffer (pH 7) containing 1.0 M and 2.0 M NaCl.

Ammonium Sulfate Precipitation

Saturated ammonium sulfate (SAS) was added into the protein eluate drop-by-drop with mixing on a vortex to a final concentration of 35% (w/v). Samples were kept on ice for 10 minutes, and centrifuged for 5 minutes at 12,000×g. The supernatant was discarded, and the pellet was prepared for subsequent analysis by sodium dodecyl sulfate-polyacrylamide gel electrophoresis (SDS-PAGE).

SDS-PAGE and Western Blot Analysis of the Purified Protein

The pellet was run on standard SDS-PAGE using a 10% gel according to the method of Laemmli. After electrophoresis, one part of the SDS-PAGE gel was transferred to nitrocellulose and the other was directly stained with Coomassie Brilliant Blue (CBB). Nitrocellulose membrane was first incubated with mouse monoclonal antibody specific for BMP-7 (Genera Research Laboratory), and kept overnight at 4° C. Alkaline phosphatase-conjugated goat anti-mouse antibody was used as secondary antibody for 1 hour at room temperature. The membrane was developed with 5 ml of a chromogenic substrate. The other part of the gel was stained with Coomassie Brilliant Blue (CBB) under standard staining procedure (0.1% CBB in 45% methanol, 10% acetic acid; 30 minutes at room temperature).

The gel was cut into slices corresponding to each protein band as revealed by staining with CBB. The gel slices were then processed to determine what proteins were present in each slice using a method of analyzing tryptic peptides released from each protein band by HPLC and mass spectrometry (MS) using a nanoelectrospray LC-MS interface as described by Olsen and Mann (*Proc. Natl. Acad. Sci. USA*, 101: 13417-13422 (2004) as modified by Grgurevic et al. (*J. Nephrol.*, 20: 311-319 (2007)). Aspects of the steps of this method that are specifically related to this study are indicated below.

In-Gel Trypsin Digestion Protocol

Bands in the gel were excised from CBB stained gels and digested with trypsin. Briefly, gel pieces were shrunk with 100 μl of acetonitrile for 8 minutes. Liquid was removed and gel pieces were re-swelled with 100 μl of ammonium hydrogencarbonate for 12 minutes and then dried in SpeedVac for 10 minutes. Dithiothreitol (DTT, 100 μl) was added and incubated for 45 minutes at 57° C. Gel pieces were shrunk with 100 μl of acetonitrile for 8 minutes at 57° C., spun down, and liquid was removed. Iodoacetamide (100 μl) was added to each gel piece and incubated for 45 minutes at room temperature in the dark without agitation. Trypsin (10 μl) was added per gel piece. Then the gel pieces were spun down and re-swelled for 10 minutes. Samples were incubated overnight at 37° C. in a thermo-mixer.

Peptide Extraction Protocol

Samples were removed from the 37° C. thermo-mixer. A solution (50 μl) containing acetonitrile, water, and formic acid was added. Samples were sonicated for 15 minutes. Supernatant was transferred to the reserve tube and 50 μl of acetonitrile were added. Extracts were dried under vacuum in the SpeedVac to complete dryness (about 40 minutes). Peptides were re-dissolved with 10 μl of solution containing water, methanol, and formic acid. Samples were sonicated for 5 minutes, and stored at −20° C. until analysis.

Mass Spectrometry

Tryptic peptides were analyzed by liquid chromatography-mass spectrometry (LC-MS) as follows. Agilent 1100 nano-flow HPLC system (Agilent Technologies, Palo Alto, Calif.) was coupled to a 7-Tesla LTQ-FT mass spectrometer (Thermo Electron, Bremen, Germany) using a nano-electrospray LC-MS interface (Proxeon Biosystems, Odense, Denmark). Peptides were separated on a home-made 75 μm $C_{18}$ HPLC column and mass-analyzed on-the-fly in the positive ion mode. Each measurement cycle consisted of a full mass spectrometry (MS) scan, followed by selected ion monitoring (SIM) scan, MS/MS, and MS/MS/MS scans of the three most intense ions. This provided a typical peptide mass accuracy of 2 ppm, as well as additional sequence information from the MS/MS and MS/MS/MS fragment ions; Resulting spectra were centroided, and searched against NCBInr database using Mascot search engine (Matrix Science). Searches were done with tryptic specificity, carboxyamidomethylation as fixed modification, and oxidized methionine as variable modification. Mass tolerance of 5 ppm and 0.6 Da was used for MS and MS/MS spectra, respectively.

Results

The LS-MS and immunoblotting analyses revealed twelve (12) tryptic peptides that were compared with the NCBInr database. The 12 peptides were found not to belong to any known osteogenic BMP, but to the splice isoform 3 of the precursor of BMP-1-3 (Swiss-Prot: P13497-2; SEQ ID NO:2), i.e., procollagen C-proteinase. The amino acid sequences of each of the 12 peptides are:

```
GGGPQAISIGK,             (amino acids 193-203 of SEQ ID NO:2)

HVSIVR,                  (amino acids 233-238 of SEQ ID NO:2)

GDIAQAR,                 (amino acids 308-314 of SEQ ID NO:2)

ISVTPGEK                 (amino acids 352-359 of SEQ ID NO:2)

LPEPIVSTDSR              (amino acids 401-411 of SEQ ID NO:2)

DGHSESSTLIGRYCGYEKPDDIK  (amino acids 497-519 of SEQ ID NO:2)

FVSDGSINK,               (amino acids 529-537 of SEQ ID NO:2)

CSCDPGYELAPDK,           (amino acids 572-584 of SEQ ID NO:2)

SGLTADSK,                (amino acids 653-660 of SEQ ID NO:2)

KPEPVLATGSR,             (amino acids 826-836 of SEQ ID NO:2)

FYSDNSVQR,               (amino acids 841-849 of SEQ ID NO:2)

FHSDDTITK.               (amino acids 958-966 of SEQ ID NO:2)
```

The 12 peptides had a combined Mascot score of 190, which presents $10^{-19}$ probability of random (false) identification.

No other protein in the NCBInr database matched the same set of peptides. No authentic osteogenic BMP proteins were detected at molecular weight of 100 kDa and 35 kDa by LS-MS or by immunoblotting.

The results indicate that authentic osteogenic BMPs do not normally circulate in the blood of healthy adult humans, whereas BMP-1-3, i.e., procollagen C-proteinase, is a soluble protein component of normal human blood.

Example 2

Osteogenic BMP cannot be isolated from human blood plasma or 24-hour urine rat sample as determined by heparin Sepharose affinity chromatography and subsequent protein identification using mass spectrometry (MS).

Plasma Collection

Blood samples from 17 healthy adults (21-50 years) were drawn into syringes containing 3.8% sodium citrate to form an anticoagulant-to-blood ratio (v/v) of 1:9 Plasma was obtained by centrifugation (15 min. at 3,000×g), and aliquots of each adult sample were used to make a pooled plasma stock. Aliquot samples were stored at −80° C. prior to analysis.

Urine Collection

A 24 hour urine sample from healthy rats (Sprague-Dawley, 5 months old, Harlan Winkelmann, Borchen, Germany) was collected in metabolic cages. Prior to purification, the urine was filtrated through Whatmann filter paper (large pore size) to remove big particles. Samples were stored at −80° C. until studied.

Affinity Column Purification of Plasma Samples

Pooled human plasma (35 ml) was diluted 2-fold with 10 mM sodium phosphate buffer (pH 7) and applied to a 5 ml heparin Sepharose column (Amersham Pharmacia Biotech), previously equilibrated with 10 mM sodium phosphate buffer (pH 7). Bound proteins were eluted from the column 10 mM sodium phosphate buffer (pH 7) containing 1.0 M and 2.0M NaCl.

Affinity Column Purification of Urine Rat Samples

A 24 hour urine rat sample (20 ml) was diluted 2-fold with 10 mM sodium phosphate buffer (pH 7), and applied to a 1 ml heparin Sepharose column (Amersham Pharmacia Biotech), previously equilibrated with 10 mM sodium phosphate buffer (pH 7). Bound proteins were eluted with 10 mM sodium phosphate buffer (pH 7) containing 1.0 M and 2.0 M NaCl.

Ammonium Sulfate Precipitation

Saturated ammonium sulfate (SAS) was added into the protein eluate drop-by-drop on the vortex until the final concentration of 35%. Samples were kept on ice for 10 minutes, and centrifuged for 5 minutes at 12,000×g. Supernatant was discarded, and pellet was prepared for subsequent SDS-PAGE analysis. The pellet was run on SDS-PAGE, and proteins in the gel analyzed as described below.

SDS-Polyacrylamide Gel Electrophoresis and Western Blot Analysis of the Purified Protein The pellet was run on standard SDS-PAGE using a 10% gel according to the method of Laemmli as described above. After electrophoresis, one part of the SDS-PAGE gel was then transferred to nitrocellulose and the other was directly stained with CBB. Nitrocellulose membrane was first incubated with mouse monoclonal antibody specific for BMP-7 (Genera Research Laboratory), and kept overnight at 4° C. Alkaline phosphatase-conjugated goat anti-mouse was used as the secondary antibody for 1 hour at room temperature. The membrane was developed with 5 ml chromogenic substrate. The other part of the gel was stained with CBB under standard staining procedure (0.1% CBB in 45% methanol, 10% acetic acid; 30 minutes at room temperature).

The gel was cut into slices corresponding to each protein band as revealed by staining with CBB. The gel slices were then processed to determine what proteins were present in each slice using the method of analyzing tryptic peptides as described above. Aspects of the steps of this method that are specifically related to this study are indicated below.

In-Gel Trypsin Digestion Protocol

Comparing the molecular weight position of bands on the gel stained with CBB with their position on the nitrocellulose membrane, bands 39 kDa, 35 kDa, and 50 kDa from the urine sample and bands 39 of kDa and 35 kDa from plasma sample were excised from CBB stained gel. Gel pieces were shrunk with 100 μl of acetonitrile for 8 minutes. Liquid was removed and gel pieces were re-swelled with 100 μl of ammonium hydrogencarbonate for 12 minutes and then dried in a Speed-Vac for 10 minutes. DTT (100 μl) was added and incubated for 45 minutes at 57° C. Gel pieces were shrunk with 100 μl of acetonitrile for 8 minutes at 57° C., spin down and liquid were removed. Iodoacetamide (100 μl) was added to each gel piece and incubated for 45 minutes at room temperature in the dark without agitation. Trypsin (10 μl) was added per gel piece. Then the pieces were spun down, and re-swelled for 10 minutes. Samples were incubated overnight at 37° C. in a thermo-mixer.

Peptide Extraction Protocol

Samples were removed from the 37° C. thermo-mixer. A solution (50 μl) containing acetonitrile, water, and formic acid was added. Samples were sonicated for 15 minutes. Supernatant was transferred into the reserve tube, and acetonitrile (50 μl) was added. Extracts were dried in the SpeedVac to complete dryness (about 40 min.). Peptides were re-dissolved with 10 μl of a solution containing water, methanol, and formic acid. Samples were sonicated for 5 minutes, and stored at −20° C. until analysis.

Mass Spectrometry (MS)

Tryptic peptides were analyzed by liquid chromatography-mass spectrometry (LC-MS) as follows: Agilent 1100 nano-flow HPLC system (Agilent Technologies, Palo Alto, Calif.) was coupled to a 7-Tesla LTQ-FT mass spectrometer (Thermo Electron, Bremen, Germany) using a nano-electrospray LC-MS interface (Proxeon Biosystems, Odense, Denmark). Peptides were separated on a home-made 75 μm $C_{18}$ HPLC column and mass-analyzed on-the-fly in the positive ion mode. Each measurement cycle consisted of a full MS scan, followed by selected ion monitoring (SIM) scan, MS/MS and MS/MS/MS scans of the three most intense ions. This has resulted in a typical peptide mass accuracy of 2 ppm, as well as additional sequence information from the MS/MS and MS/MS/MS fragment ions.

Resulting spectra were centroided, and searched against NCBInr database using Mascot search engine (Matrix Science). Searches were done with tryptic specificity, carboxyamidomethylation as fixed modification, and oxidized methionine as variable modification. Mass tolerance of 5 ppm and 0.6 Da was used for MS and MS/MS spectra, respectively.

Results

No authentic, osteogenic BMPs were detected in any of the proteins isolated from the entire molecular range of purified sera from normal healthy individuals or from urine of rats by mass spectrometry or by Western blotting.

Example 3

Lack of ectopic bone formation by implantation of lyophilized human blood samples into nude mice and autologous rat lyophilized blood samples into rat.

Blood Collection

Blood (50 ml) was collected from 10 healthy human individuals. The blood was centrifuged to remove cells, and the serum was stored at −20° C. until analyzed. Autologous blood (5 ml) was collected from ten 6-months old male Sprague Dawley rats at five time intervals in a period of two weeks. Samples were centrifuged and the serum was stored at −20° C. until analyzed.

Implantation into Nude Mice and Rats

One bone pellet was formed by mixing 100 mg of human lyophilized blood with 200 mg of demineralized rat bone matrix (DBM) and implanted into the back area of nude mice. In addition, 20 mg of autologous rat lyophilized blood was mixed with 100 mg of DBM and implanted subcutaneously into the axillar area of the same rats from which the blood had been drawn. Pellets were removed three weeks following implantation, fixed and processed for histology.

Results

Tested blood samples implanted under the skin of nude mice were negative for bone formation, indicating that blood does not contain authentic osteogenic BMPs in an amount that could induce ectopic bone formation in mice and rats.

Example 4

Unlike recombinant human BMP-7, systemically administered BMP-1-1 does not induce bone formation in an ectopic bone formation assay.

Bone pellets consisting of demineralized bone matrix (100 μg) were implanted subcutaneously (ectopic site) into 20 adult Sprague Dawley rats in the axillar region as described previously (Simic et al, *J Biol. Chem.,* 281:13514 (2006)). Ten rats were then injected intravenously with 20 μg of recombinant human BMP-7 from days 2 to 7 following implantation, while another ten rats were injected on a similar schedule with recombinant human BMP-1-1. Two weeks following implantation, the pellets were removed and processed for histological evaluation.

Results

In pellets of rats injected with the BMP-7, cartilage and bone were formed via a mechanism which involved binding of BMP-7 to the implanted DBM and induction of endochondral bone formation cascade as previously described (Simic et al, supra). In contrast, in the pellets of rats treated systemically with BMP-1-1, there was no cartilage or bone detected, indicating that BMP-1-1 cannot induce bone at an ectopic site.

The results indicate that unlike authentic osteogenic BMP-7, systemically administered BMP-1-1 cannot induce bone formation in an ectopic bone formation assay.

Example 5

Cloning and sequence analysis of cDNA encoding BMP-isoforms from human placental cDNA library.

The cDNA comprising the coding sequences for BMP-1-1, BMP-1-3, BMP-14, and BMP-1-7 were cloned from a human placental cDNA library using the GATEWAY® recombination cloning and expression system (Invitrogen, Carlsbad, Calif.). The correctness of clones was confirmed by standard colony PCR and restriction enzyme analysis.

The nucleotide base sequences of the cDNA clones were determined and the corresponding amino acid sequences deduced. The amino acid sequence for the 83 kDa BMP-1-1 is shown in SEQ ID NO:1. The nucleotide base sequence of the cDNA clone encoding the BMP-1-3 isoform is shown in SEQ ID NO:3 and the corresponding amino acid sequence for the 111 kDa BMP-1-3 isoform is shown in SEQ ID NO:2. The amino acid sequence for the 91 kDa BMP-1-7 isoform is shown in SEQ ID NO:7.

The nucleotide base and corresponding amino acid sequences as determined for the cDNA clone in this study for the BMP-1-1 and BMP-1-7 isoforms were found to be identical to those present in the EMBL and Swiss-Prot databases. However, the cDNA sequence for the BMP-1-3 clone as determined herein differs at a single nucleotide base from that in the EMBL database. In particular, the EMBL reference sequence (SEQ ID NO:3) has a thymine (T) base at position 1487, whereas the sequence of cloned BMP-1-3 cDNA (SEQ ID NO:5) has an adenine (A), which in turn results in a codon change of a CTG (leucine) in the EMBL sequence to a CAG (glutamine) in the placental BMP-1-3 cDNA sequence isolated by us. Thus, the amino acid sequence of the Swiss-Prot database for BMP-1-3 (SEQ ID NO:2) contains a leucine residue at position 493, whereas the amino acid sequence of the placental BMP-1-3 protein (SEQ ID NO:4) encoded by the isolated cDNA clone contains glutamine at position 493.

Site-directed mutagenesis was performed on the placental BMP-1-3 protein of the isolated cDNA clone to convert base 1478 of its reported sequence (SEQ ID NO:3), i.e., a switch from adenine (A) to thymine (T). On expression, this yielded a "converted" protein of BMP-1-3 having the amino acid sequence of SEQ ID NO: 2.

Results

The placental BMP-1-3 protein, which has the amino acid sequence of SEQ ID NO:4 when expressed from the library-isolated cDNA clone, and the "converted" BMP-1-3 protein, which has the amino acid sequence as reported in the Swiss-Prot database (SEQ ID NO:2), were both active in processing in vitro procollagen type I, II, and III, with the "converted" BMP-1-3 protein being more active at lower concentrations. However, the placental BMP-1-3 expressed from the isolated cDNA clone processed calmodulin and type IV collagen, which properties were not exhibited with the "converted" BMP-1-3 protein. Accordingly, the BMP-1-3 isoform expressed from the cloned cDNA of the placental library differs in both amino acid sequence and functional enzymatic properties from the BMP-1-3 protein reported in the Swiss-Prot database.

Example 6

Several specific BMP-1 isoforms circulate in human blood in different diseases.

Plasma Collection

Blood samples were drawn from 10 healthy adults, from 10 patients each who were diagnosed and undergoing treatment for diseases including acute pancreatitis, cirrhosis, acute bone fracture, chronic renal failure on dialysis, and from 4 patients with rare bone diseases, namely fibrodysplasia ossificans progressive (FOP) and osteogenesis imperfecta (OI). The blood samples were drawn into syringes containing 3.8% sodium citrate to form an anticoagulant-to-blood ratio (v/v)

of 1:9. Plasma was obtained by centrifugation (15 minutes at 3000×g), and aliquots of each blood sample were used to make a pooled plasma stock to represent each of the listed normal or pathological cases. Aliquot samples were stored at −80° C. prior to analysis.

Affinity Column Purification 80 ml of pooled human plasma from each group of patients was diluted 2-fold with 10 mM sodium phosphate buffer (pH 7), and applied to a 5 ml heparin Sepharose column (Amersham Pharmacia Biotech), previously equilibrated with 10 mM sodium phosphate buffer (pH 7). Bound proteins were eluted from the column with 10 mM sodium phosphate buffer (pH 7) containing 1.0 M and 2.0 M NaCl.

Ammonium Sulfate Precipitation

Saturated ammonium sulfate (SAS) was added into the protein eluate drop-by-drop on the vortex until the final concentration of 35%. Samples were kept on ice for 10 minutes, and centrifuged for 5 minutes at 12,000×g. Supernatant was discarded, and pellet was prepared for subsequent SDS-PAGE analysis.

SDS-PAGE and Western Blot Analysis of the Purified Protein

The pellet was run on standard SDS-PAGE on a 10% gel according to the method of Laemmli. After electrophoresis, one part of the SDS-PAGE gel was then transferred to nitrocellulose and the other was directly stained with Coomassie Brilliant Blue (CBB).

Nitrocellulose membrane was first incubated with rabbit polyclonal antibody specific for the BMP-1 carboxyl terminal domain (Sigma-Aldrich, Chemie GmbH, Germany), and kept overnight at 4° C. Alkaline phosphatase-conjugated anti-rabbit antibody (Invitrogen Corporation Carlsbad, SAD) was used as secondary antibody for 1 hour at room temperature. The membrane was developed with 5 ml chromogenic substrate.

The other part of the gel was stained under standard staining procedure (0.1% CBB in 45% methanol, 10% acetic acid; 30 minutes at room temperature).

The gel was cut into slices corresponding to each protein band as revealed by staining with CBB. The gel slices were then processed to determine what proteins were present in each slice using a method of analyzing tryptic peptides as described above. Aspects of the steps of this method that are specifically related to this study are indicated below.

In-Gel Trypsin Digestion Protocol

Gel pieces were shrunk with 100 µl of acetonitrile for 8 minutes at 57° C., spun down, and liquid was removed. Gel pieces were re-swelled with 100 µl of ammonium hydrogencarbonate for 12 minutes and then dried in a SpeedVac for 10 minutes. DTT (100 µl) was added and incubated for 45 minutes at 57° C. Iodoacetamide (100 µl) was added to each gel piece and incubated for 45 minutes at room temperature in the dark without agitation. Trypsin (10 µl) was added per gel piece, spun down, and gel pieces were re-swelled for 10 minutes. Samples were incubated overnight at 37° C. on a thermo-mixer.

Peptide Extraction Protocol

Samples were removed from the 37° C. thermo-mixer. A solution (50 µl) containing acetonitrile, water, and formic acid was added. Samples were sonicated for 15 minutes. Supernatant was transferred into the reserve tube, and acetonitrile (50 µl) was added. Extracts were dried in the SpeedVac to complete dryness (about 40 minutes). Peptides were redissolved with 10 µl of a solution containing water, methanol and formic acid. Samples were sonicated for 5 minutes, and stored at −20° C. until analysis.

Mass Spectrometry

Tryptic peptides were analyzed by liquid chromatography-mass spectrometry (LC-MS) as follows: Agilent 1100 nano-flow HPLC system (Agilent Technologies, Palo Alto, Calif.) was coupled to a 7-Tesla LTQ-FT mass spectrometer (Thermo Electron, Bremen, Germany) using a nano-electrospray LC-MS interface (Proxeon Biosystems, Odense, Denmark). Peptides were separated on a home-made 75 µm $C_{18}$ HPLC column and mass-analyzed on-the-fly in the positive ion mode. Each measurement cycle consisted of a full MS scan, followed by selected ion monitoring (SIM) scan, MS/MS and MS/MS/MS scans of the three most intense ions. This resulted in a typical peptide mass accuracy of 2 ppm, as well as additional sequence information from the MS/MS and MS/MS/MS fragment ions.

Resulting spectra were centroided, and searched against NCBInr database using Mascot search engine (Matrix Science). Searches were done with tryptic specificity, carboxyamidomethylation as fixed modification, and oxidized methionine as variable modification. Mass tolerance of 5 ppm and 0.6 Da was used for MS and MS/MS spectra, respectively.

Results

The results of this study are shown in Table 1 (supra), which provides profiles of circulating BMP-1 isoforms associated with normal health and the indicated disorders. The results indicate that the BMP-1-3 isoform is normally present in the blood of healthy individuals but disappears from circulation in patients with acute bone fracture, cirrhosis, and acute pancreatitis. It was surprisingly noted that in FOP and OI patients BMP-1-3 isoform was still present, but present at more than ten times the level observed in the blood of healthy individuals.

Disappearance of the BMP-1-3 isoform from the circulation of patients with acute bone fracture confirms the potential function of BMP-1 isoforms in processing the ECM proteins in bone regeneration and repair during the formation of callus during the rebridgement of fractured bone ends. Disappearance of BMP-1-3 from circulation in patients with cirrhosis suggests its involvement in processes related to fibrotic changes in the liver. In acute pancreatitis, several ECM molecules involved in the pathophysiology of the disease eventually require the BMP-1-3 for processing of ECM molecules.

The sera from patients with acute pancreatitis were collected at an early stage of the disease, i.e., prior to robust serum elevation of the pancreatic enzymes such as pancreatic amylase and lipase. Surprisingly, the blood of these patients contained the BMP-1-7 isoform, which has not been previously detected at the protein level.

The BMP-1-5 isoform was found only in patients with chronic kidney failure on dialysis, which suggests a specific function for this enzyme isoform, e.g., involvement in the fibrotic processes in bone called renal osteodystrophy. Interestingly, this is also the first demonstration of BMP-1-5 isoform on the protein level. Previously, the BMP-1-5 isoform was inferred only at the level of tissue mRNA transcripts.

The presence of BMP-1-3 isoform in circulation was further confirmed by Western blot using a specific BMP-1-3 antibody developed by Genera (data not shown).

Example 7

Protection of kidney function in ischemic acute renal failure in rats by inhibiting circulating BMP-1-1 and BMP-1-3 prior to ischemia/reperfusion.

Animals

Female Sprague-Dawley rats weighting about 350-400 g were housed and allowed free access to water and food.

Ischemia/Reperfusion Model

Rats were anesthetized with 100 mg/kg ketamine, 10 mg/kg xylazine, and 1 mg/kg acepromazine (intramuscularly, im) and placed on a heating table kept at 37° C. A midline incision was made and both renal pedicles were clamped for 60 minutes. After removal of the clamp, 5 ml of prewarmed normal saline were instilled into the peritoneal cavity, and the incision was sutured. A total of 24 animals were assigned to two different experimental groups:

Group 1. Control group (n=12); ischemia/reperfusion model without therapy (administered physiological saline vehicle, pH 7.2, only)

Group 2. Antibody treatment group (n=12); ischemia/reperfusion model+16 µg of anti-BMP-1-1 antibody (c=1 µg/µl) and 16 µg of anti-BMP-1-3 antibody (c=1 µg/µl) prior to ischemia/reperfusion and then for 5 days after ischemia/reperfusion.

Blood samples were obtained before occlusion and at 0, 24, 72, 96, 120, and 168 hours after reperfusion. The plasma was separated by centrifugation renal function parameters were measured. Rats were killed at day 7 after reperfusion and kidneys were harvested for histological analysis. Therapy was applied in a prophylactic mode at 2 hours prior to clamping and then following the release of the clamps for five days thereafter.

Assessment of Renal Function

Blood samples (0.5 ml) were obtained from the orbital venous plexus at 0, 24, 72, 96, 120, and 168 hours after ischemia. Serum creatinine was measured by Jaffe method (alkaline picrate) and blood urea nitrogen (BUN) by enzymatic glutamate dehydrogenase-UV procedure as previously described (Vukicevic et al., *J. Clin. Invest.*, 102: 202-214 (1998)). The cumulative survival rate was observed and recorded for both control and experimental rats.

Renal Morphology

Kidneys for histological examination were fixed in 2% paraformaldehyde, and 7 µm paraffin sections were cut and stained with haematoxylin and eosin. Tubulointestinal injury, defined as tubular dilatation and/or atrophy, interstitial fibrosis and inflammatory cell infiltrate, as well as glomerular damage were graded using a semi-quantitative scale from 0 to 4 according to the following criteria: 0=no changes; 1=focal changes involving 1-25% of the samples; 2=changes affecting 26-50% of the sample; 3=changes involving 51-75% of the sample; and 4 lesions affecting more than 75% of the sample as previously described (Vukicevic et al., *J. Clin. Invest.*, id.). Two independent observers performed histologic studies in a blinded fashion.

Results

Creatinine levels in blood from rats of the untreated control group (Group 1, no antibody therapy) and from rats of the treatment group (Group 2, antibodies against BMP-1-1 and BMP-1-3) are shown in FIG. 1. In control rats, following a 60-minute clamping of both kidneys followed by reperfusion, the creatinine (FIG. 1, diagonal line bars) and BUN (not shown) rose sharply and remained high at 24 hours (1 day) and 72 hours (3 days) following ischemia, then showed normalization at day 7 in animals that survived the procedure. When antibodies to BMP-1-1 and BMP-1-3 were administered (Group 2) prior to ischemia and then for five days following ischemia, both the creatinine (FIG. 1, stippled bars) and BUN (not shown) values remained low. The survival rate was 35% in rats of the control group (no antibody therapy) and 55% in rats treated with antibodies to BMP-1-1 and BMP-1-3 prior to and following ischemia/reperfusion (data not shown). As observed on the histology slides (FIG. 2), kidneys of rats of the control group that were exposed to ischemia/reperfusion injury without antibody therapy had lost the structural integrity in more than 75% of the kidney area with dilated proximal and distal tubules, had lost the tubular epithelium, and about 30% of the entire kidney area was undergoing fibrotic healing due to necrosis (see, FIG. 2, Panel 2A). In contrast, sections of kidney tissue from rats that received antibodies to BMP-1-1 and BMP-1-3 prior to ischemia/reperfusion injury indicated significant preservation of kidney structures (see, FIG. 2, Panel 2B).

These results show that the severity of damage to kidney structure that would otherwise occur as the result of an ischemic/reperfusion event can be prevented by a regimen of systemic administration of neutralizing antibodies to the BMP-1-1 and BMP-1-3 isoforms prior to the ischemia/reperfusion event.

Example 8

Enhancing survival by systemic administration of BMP-1 isoform following ischemic acute renal failure in rats.

Animals

Female Sprague-Dawley rats weighting about 300 g-400 g were housed and allowed free access to water and food.

Ischemia/Reperfusion Model

Rats were anesthetized with 100 mg/kg ketamine, 10 mg/kg xylazine, and 1 mg/kg acepromazine (im) and placed on a heating table kept at 37° C. A midline incision was made, and both renal pedicles were clamped for 60 min. After removal of the clamp, 5 ml of normal saline were instilled into the peritoneal cavity and the incision was sutured. A total of 24 animals were assigned to four different experimental groups:

Group 1. Negative control group (n=12); ischemia/reperfusion model without therapy.

Group 2. Positive control group ("BMP-7") (n=8); 100 µg/kg BMP-7 for five days.

Group 3. BMP-1-1 treatment group ("BBM-1-1") (n=8); 4 µg of BMP1-1 (c=0.2 µg/µl) for five days.

Group 4. BMP-1-1 antibody treatment group ("BMP-1 Ab") (n=8); 16 µg of anti-BMP-1-1 antibody (c=1 µg/µl) for five days after release of clamps (post ischemia/reperfusion event).

Blood samples were obtained before occlusion and at 0, 24, 72, 96, 120, and 168 hours after reperfusion. The plasma was separated by centrifugation. These samples were used for measurement of renal function parameters. Rats were killed at day 7 after reperfusion, and kidneys were harvested for histological analysis. Therapy was applied following clamping and for five days thereafter.

Assessment of Renal Function

Blood samples (0.5 ml) were obtained from the orbital venous plexus at 0, 24, 72, 96, 120, and 168 hours after ischemia. Serum creatinine was measured by Jaffe method (alkaline picrate) and blood urea nitrogen (BUN) by enzymatic glutamate dehydrogenase-UV procedure as previously described. The cumulative survival rate was observed and recorded for both control and experimental rats.

Results

Figure 3:
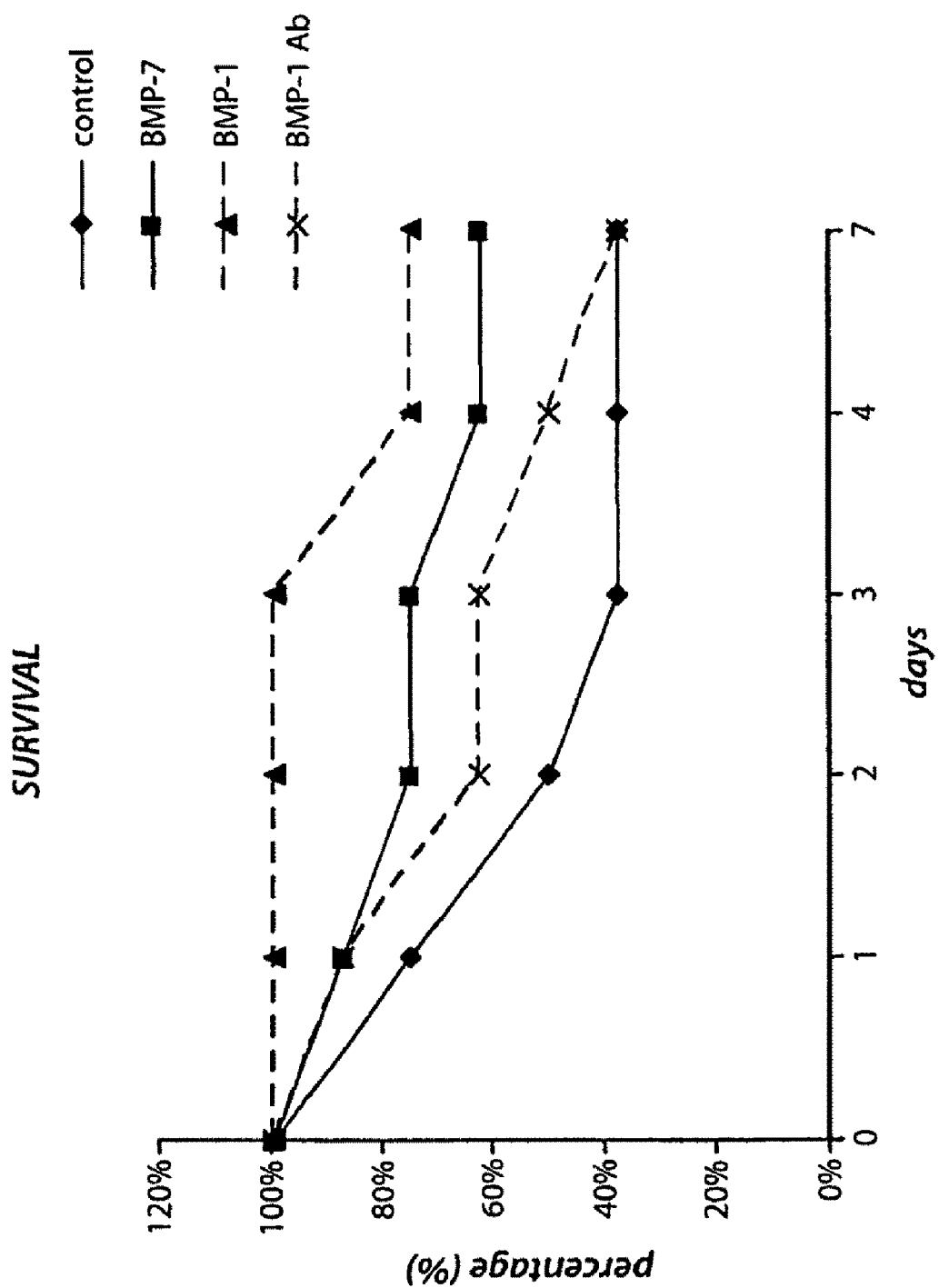
FIG. 3 shows a graph of the percent survival of rats over time (days) after ischemic acute renal failure injury as described in Example 8, below. Diamonds (♦, "control") show survival of rats in the negative control group that did not receive therapy after ischemia/reperfusion injury. Squares (■, "BMP-7") show survival of rats in the positive control group that received BMP-7, a known therapeutic agent for treatment of ischemia/reperfusion injury in kidney. Triangles (▲, "BMP-1") show survival of rats that received BMP-1-1 after injury. Diagonal crosses (x, "BMP-1 Ab") show survival of rats that received antibody to BMP-1-1 after injury. The results indicate that administration of BMP-1-1 isoform after injury increased the survival rate of rats with ischemia/reperfusion acute renal failure. See, Example 8, for details.
Figure 5A:
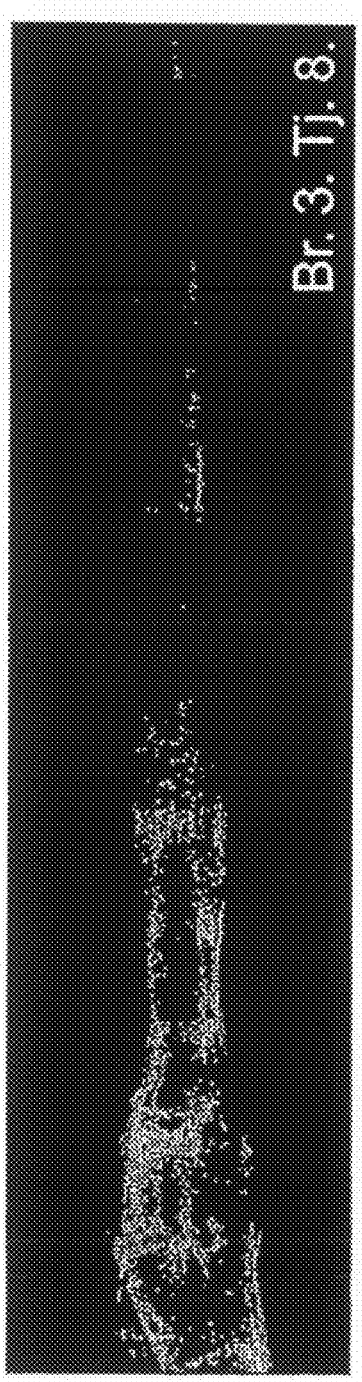
FIGS. 5A and 5B show ulnar defect in representative bone after 6 weeks from rabbits of a control group treated locally with a whole blood-derived coagulum device (WBCD) only, without BMP-1 isoform or BMP-7, as described in Example 14, below.
Figure 5B:
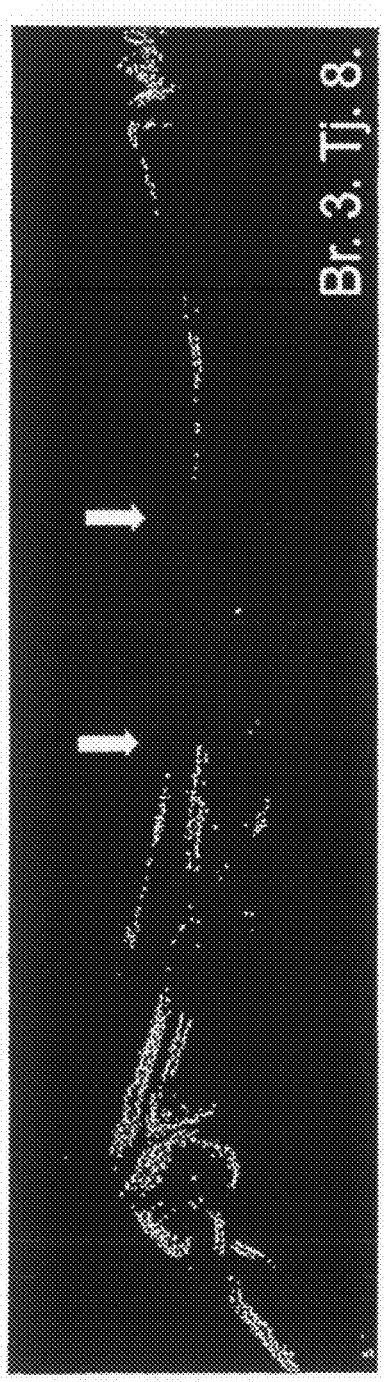

Survival of rats in the various treatment groups is shown in FIG. 3. In negative control rats (Group 1, no therapy) following a 60-minute clamping of both kidneys followed by a reperfusion, levels of creatinine and BUN rose sharply (not shown), and greater than 60% of the animals did not survive (see, FIG. 3, diamond data points). Administering BMP-1-1 immediately following reperfusion ("BMP-1-1" group) significantly decreased the mortality and maintained the survival rate at 80% compared to the 40% survival rate of untreated negative control rats (see, FIG. 3, triangle data points).

Although higher at days 2 and 3 in BMP-1-1 treated rats, serum creatinine levels sharply declined on day 4 (data not shown), probably due to a rapid processing of extracellular matrix in the thrombotic area and a relatively fast recovery of the structural elements that prevented significant necrosis due to accumulation of the fibrotic post-necrotic tissue. Administration of the BMP-1-1 antibody ("BMP-1 Ab") for five days following the removal of the clamps (see, FIG. 3, cross data points) was not effective in preventing a high mortality rate (i.e., as low as 40% survival rate at day 7 as seen also in the untreated control group).

The results of this experiment indicate that the administration of a recombinant BMP-1 isoform following ischemic acute renal failure is effective to reduce structural damage to the kidney and to increase survival rate of the affected individual.

Example 9

Delaying progression of chronic renal failure (CRF) in rats by inhibiting BMP-1 isoforms.

Animals

Female Sprague-Dawley rats weighting about 350-400 g were housed and allowed free access to water and food.

5/6 Nephrectomy (Nx) Model of CRF

Rats were anesthetized with 100 mg/kg ketamine, 10 mg/kg xylazine, and 1 mg/kg acepromazine (im) and placed on a heating table kept at 37° C. A midline incision was made, and both renal pedicles were clamped for 60 min. The left kidney was removed, and the rats were left for a week to recover. Then, ⅚ of the right kidney mass was removed, and rats were left to recover for a period of two weeks. A total of 88 animals were assigned to 4 different experimental groups:

Group 1. Control group (n=12); 5/6 Nx rats receiving the physiological vehicle solution.

Group 2. BMP-1-1 antibody group (n=12); Nx+16 μg of BMP-1-1 antibody (c=1 μg/μl) weekly for a period of 12 weeks Group 3. BMP-1-3 antibody group (n=12); Nx+16 μg of BMP-1-3 antibody (c=1 μg/μl) weekly for a period of 12 weeks Group 4. BMP-1-1+BMP-1-3 antibody group (n=12); Nx+16 μg of BMP1-1 antibody (c=1 μg/μl) weekly for a period of 12 weeks and 16 μg of BMP-1-3 antibody (c=1 μg/μl) weekly for a period of 12 weeks.

Blood samples were obtained before surgery and then weekly throughout the duration of the experiment. Rats were killed at 12 weeks following the removal of the right kidney mass. Therapy was applied intravenously (iv) weekly for a period of 12 weeks.

Assessment of Renal Function

Blood samples (0.5 ml) were obtained from the orbital venous plexus weekly. Serum creatinine was measured by Jaffe method (alkaline picrate) and blood urea nitrogen (BUN) by enzymatic glutamate dehydrogenase-UV procedure as previously described (Vukicevic et al., *J. Clin. Invest.*, op. cit.). The cumulative survival rate was observed and recorded for both control and experimental rats.

Renal Morphology

Kidneys for histological examination were fixed in 2% paraformaldehyde, and 7 μm paraffin sections were cut and stained with haematoxylin and eosin. Kidney damage was graded as described (Borovecki et al., in *Bone morphogenetic proteins—Bone regeneration and beyond*, edited by Vukicevic S. and Sampath K. T., 2002). Briefly, the structure of glomeruli, kidney tubules, and the amount of interstitial fibrosis were measured on the kidney area using an automated computer program. The measured parameters were expressed as a number of vital versus damaged glomeruli and as a percent of fibrotically altered kidney area. Two independent observers performed histologic studies in a blinded fashion.

Results

Following 12 weeks of therapy, control rats (Group 1), which received only the vehicle solution, had creatinine values above 300 mEq/L. Animals treated with a single antibody, i.e., antibody to BMP-1-1 (Group 2) or antibody to BMP-1-3 (Group 3), or with a combination of both antibodies (Group 4) had significantly lower creatinine serum values as compared to control rats. In particular, rats treated with anti-BMP-1-1 antibody (Group 2) or with anti-BMP-1-3 antibody (Group 3) had, respectively, 36% and 39% lower creatinine serum values than control rats. Creatinine serum values were 54% lower in rats treated with a combination of both anti-BMP1-1 and anti-BMP-1-3 antibodies than in the control rats. In animals treated with a combination of both antibodies (Group 4), the fibrotic area was reduced by 57% relative to control rats, while in rats treated with only the anti-BMP-1-1 antibody (Group 2) or with only the anti-BMP-1-3 antibody (Group 3), the fibrotic area was reduce by 23% and 16%, respectively. In addition, the fibrotic area was reduced by 43% in rats treated with a combination of both antibodies as compared to rats treated with BMP-7, a positive control.

These results indicate that inhibition of BMP-1-1 and BMP-1-3 in a model of a chronic renal failure (CRF) delayed the progression of the disease by maintaining the structural integrity of glomeruli and preventing accumulation of fibrotic tissues, thus, improving the kidney function by about 50% in a period of 12 weeks following CRF. This relates to increasing a human life span by about 120 months or about 10 years.

Example 10

Acceleration of fracture repair with systemically administered BMP-1-1 and localization of BMP-1-1 at orthotopic site of bone fraction.

Animals and Experimental Protocol

Fifty (50) 4-month old Sprague-Dawley female rats were used in this study. Animals weighed approximately 300 grams (g). They were kept in standard conditions (24° C., 12 hour/12 hour light/dark cycle) in 20×32×20 cm cages during the study and were allowed free access to water and pelleted commercial diet (Harlan Teklad, Borchen, Germany). Rats were divided into three treatment groups and two control groups:

Group 1. Control rats (10) were treated with a Kirschner wire following surgically produced fracture and then treated systemically with a vehicle solution (physiological saline, pH 7.2) only.

Group 2. Rats treated with BMP-1-1 (10 μg/kg) for a period of one week. Ten rats were treated with Kirschner wire following fracture of the femur and then intravenously treated with BMP-1-1.

Group 3. Rats treated with BMP-1-1 (10 μg/μg) for a period of three weeks. Ten rats were treated with Kirschner wire following fracture of the femur and then intravenously treated with BMP-1-1.

Group 4: Rats treated with BMP-1-1 (10 μg/kg) for a period of five weeks. Ten rats were treated with Kirschner wire following fracture of the femur and then intravenously treated with BMP-1-1.

Group 5: Positive control. Ten rats were treated with a Kirschner wire following fracture of the femur and then injected systemically with 100 μg/kg of BMP-7 for a period of five (5) weeks.

Anesthetized rats were prepared for surgery by shaving and cleaning the lower extremities. With a medial peripatellar incision, the patella was dislocated laterally exposing the femoral condyle. A Kirschner wire (1.1 mm in diameter and 2.7 cm long) was introduced into the intramedullary canal through the intercondylar notch. The Kirschner wire did not protrude into the knee joint or interfere with motion of the patella. After closing the knee joint, the mid-diaphysis of the pinned right femur was fractured by applying a bending force, as described by Bonarens and Einhorn (*J. Orthop. Res.*, 97:101 (1984)). Radiographs were obtained immediately after surgery, and rats with proximal or distal fractures were excluded from this experiment so that only mid-diaphyseal fractures were included in this study.

All animals were sacrificed following seven weeks of therapy. Radiographs were taken at week one and seven following surgery in two planes: AP (anterior-posterior) and LL (latero-lateral).

Biodistribution and Pharmacokinetics of $^{125}$I-Labeled BMP-1-1 ($^{125}$I-BMP-1-1)

Recombinant human BMP-1-1 was radioiodinated with 5 mCi of carrier-free Na $^{125}$I using a modification of the lactoperoxidase method. Gel filtration on a Sephadex G-25 column was used to separate radioiodinated BMP-1-1 ($^{125}$I-BMP-1-1) from the free iodide. The column was eluted with 20 mM sodium acetate buffer, pH 4.5 containing 0.2% Tween-80 and 0.1% ovalbumin. The specific activity of the $^{125}$I-BMP-1-1 preparation used in this study was 0.273 mCi/mg. Rats (n=10) received a single injection of $^{125}$I-BMP-1-1 at a dose level of 10 μg/kg with the activity of 20 μCi. Injection volume was 500 μl. Animals were sacrificed 30 minutes, 1, 3, 6 and 24 hours following injection. Tissues were removed, weighed, and radioactivity was measured in a gamma counter. The relative uptake of $^{125}$I-BMP-1 by tissues during time was expressed as nanograms (ng) of $^{125}$I-BMP-1 per gram (g) wet tissue weight. The experiments were also performed in five rats with acutely fractured femurs on day five following surgical osteotomy of the femur.

In Vivo and Ex Vivo Bone Mineral Density (BMD) Measurement by DXA

At two-week intervals (in period of 10 weeks), the animals were scanned for bone density measurements by dual-energy X-ray absorptiometry (DXA; Hologic QDR-4000, Hologic, Waltham, Mass.). At the end of the experiment, animals were anesthetized, weighed, and euthanized. The right femur was removed and fixed in 70% ethanol and was used for determination of the bone mineral content (BMC) and BMD by DXA equipped with Regional High Resolution Scan software. The scan field size was 5.08×1.902 cm, resolution was 0.0254× 0.0127 cm, and the speed was 7.25 mm/s. The scan images were analyzed and the bone area, bone mineral content, and bone density of whole bone.

PQCT

Isolated femurs were scanned by a peripheral quantitative computerized tomography (PQCT) X-ray machine (Stratec XCT Research M; Norland Medical Systems, Fort Atkinson, Wis.) with software version 5.40. Volumetric content, density, and area of the total bone, trabecular, and cortical regions were determined.

MicroCT

The microcomputerized tomography (MicroCT) apparatus (μCT40) and the analyzing software used in these experiments were obtained from SCANCO Medical AG (Bassersdorf, Switzerland). The right femur was scanned in 250 slices, each 13 μm thick in the dorsoventral direction. Three-dimensional reconstruction of bone was performed using the triangulation algorithm. The trabecular bone volume (BV, mm$^3$), trabecular number (Tb. N, 1/mm), the trabecular thickness (Tb. Th, μm), and the trabecular separation (Tb. Sp, μm) were directly measured on 3-dimensional (3D) images using the method described by Hildebrand et al. (*Comp. Meth. Biochem. Biomed. Eng.*, 1: 15 (1999)). The trabecular bone pattern factor (TBPf) and the structure model index (SMI) were computed using software provided with the microCT machine.

Histology

The femur was removed for histologic analyses, embedded in paraffin, cut in 10 μm thick sections, stained with hemalaun-eosin and toluidine blue.

Results

Radioactively labeled BMP-1-1 was injected intravenously into healthy rats and into rats with fractured femurs. In healthy animals, radioactive BMP-1-1 accumulated predominantly in the liver (23%), bones (31%), and muscles (9%). In rats with a fracture, 80% of injected BMP-1-1 accumulated at the fracture site.

Rats treated with BMP-1-1 for one week with daily intravenous injections showed 43% accelerated bone regeneration, which was calculated based on a scoring system of bone repair as previously described (Paralkar et al., *Proc. Natl. Acad. Sci. USA,* 100: 6736 (2003)). The formed callus was bigger by 43% in rats treated with BMP-1 for one week, and it was increased by 63% and 71% in rats treated with BMP-1 for three to five weeks, respectively. The bone healing was accelerated by 40-80% in rats treated with BMP-1-1 for a period of one or five weeks, respectively, as evidenced by full rebridgement of the three or four cortices of rat femurs.

In vivo bone mineral density measurement showed increased accumulation of mineral in the formed callus, while PQCT analyses showed increased mineral accumulation on the cortical bone of fractured femurs. MicroCT measurement showed increased accumulation of newly formed trabeculi in the regenerating fracture at seven weeks following surgical osteotomy.

These results of this study of acute femur fracture in rats collectively indicate that the vast majority (e.g., about 80%) of systemically administered BMP-1-1 becomes localized in the orthotopic site of a bone fracture and that systemically administered BMP-1-1 is effective at accelerating healing of such acute fractured femurs.

Example 11

Systemically administered BMP-1-1 into rats with fractured femur

Employing similar procedures as in Example 10, above, a study was made to compare the effect of systemic administration of BMP-1-1 isoform, BMP-7, and antibody to the BMP-1-1 isoform on healing of fractured femurs in rats.

At 4 weeks following fracture, the callus at the fracture site in rats treated systemically with BMP-1 isoform was about 20% bigger than that in untreated control rats and about 90% bigger than in rats treated systemically with BMP-7.

Results at 8 weeks following fracture are shown in FIG. 4. The area of the fracture is encircled in each of the pictured femurs FIGS. 4A-4F. Systemic administration of BMP-1-1 to rats with a fractured femur resulted in accelerated healing as compared to systemic administration of BMP-7. The fracture line had almost disappeared, and the cortical bone had rebridged in rats treated systemically with BMP-1-1 (see, bones 4A and 4D in FIG. 4), whereas the fracture line was still visible in rats treated systemically with BMP-7 (see, bones 4B, 4C, and 4E in FIG. 4). Systemic administration of neutralizing antibody to BMP-1-1 delayed fracture healing (see, bone 4F in FIG. 4).

The results indicate that systemic administration of a BMP-1 isoform is an effective method for treating bone defects.

Example 12

Locally administered BMP-1-1 into rats with fractured femur.

Animal Model of Fracture

Twenty four (24) 3-month old Sprague-Dawley male rats (350 g), were treated with Kirschner wire following fracture of the femur. Rats were divided into the following three treatment groups:

Group 1. Control rats (8) were treated with a whole (autologous) blood-derived coagulum device containing vehicle solution only (physiological solution; no BMP-1-1, no BMP-7).

Group 2. Rats treated locally with whole blood-derived coagulum device containing BMP-1 (10 μg/kg of BMP-1-1).

Group 3. Rats (8) treated with whole blood-derived coagulum device containing BMP-7 (10 μg/kg).

All animals were sacrificed seven weeks after surgery. Radiographs were taken at week 1, 4, and 7 in two planes, i.e., AP (anterior-posterior) and LL (latero-lateral).

Anesthetized rats were prepared for surgery by shaving and cleaning the lower extremities. With a medial peripatellar incision, the patella was dislocated laterally exposing the femoral condyle. A Kirschner wire (1.1 mm in diameter and 2.7 cm long) was introduced into the intramedullary canal through the intercondylar notch. The Kirschner wire did not protrude into the knee joint or interfere with motion of the patella. After closing the knee joint, the mid-diaphysis of the pinned right femur was fractured by applying a bending force, as described by Bonarens and Einhorn (*J. Orthop. Res.*, 97: 101 (1984)). Radiographs were obtained immediately after surgery, and rats with proximal or distal fractures were excluded from this experiment, so that the only mid-diaphyseal fractures were included in this study.

Preparation of Whole Blood-Derived Coagulum Device (WBCD) Containing BMP-1

Whole blood-derived coagulum devices (WBCDs) for treating bone fractures were prepared to treat bone fractures in rat femurs. Briefly, 1 ml of autologous whole blood was drawn from the orbital plexus of each rat. The whole blood was then combined with a thrombin-fibrin reagent, 1 M exogenous calcium chloride, and the indicated amount of BMP-1-1 or BMP-7, and then incubated at room temperature for 30-45 minutes to permit coagulum formation prior to implantation into the fractured femur of the rat that provided the corresponding autologous blood.

Biomechanical Testing

Femurs from both sides were removed for biomechanical testing, which included three-point bending as previously described (Simic et al., *J. Biol. Chem.*, 281: 13472 (2006)). The healthy bones from the contra-lateral side were used as positive controls. Both three-point bending test and the indentation test were used for measuring biomechanical characteristics of both the cortical and the trabecular bone.

Results

Radiographic analysis of X-rays showed that in rats treated with a WBCD containing only the vehicle solution (no BMP-1-1, no BMP-7) as a control at 4 weeks following surgery, 0.6±0.03 cortices healed, while at seven weeks following surgery 1.8±0.4 cortices healed. The callus area was 24.3±7.8 mm$^2$ at four weeks and 18.7±6.4 mm$^2$ at seven weeks.

In rats treated with a whole blood-derived coagulum device+BMP-1-1 at four weeks 1.3±0.5 (t-test, P>0.01 vs control) cortices healed, while at seven weeks 2.9±0.9 (t-test, P>0.01) cortices healed. The callus area was 13.4±4.7 mm$^2$ (t-test, P>0.01 vs control), and at seven weeks it was 7.6±3.8 mm$^2$ (t-test, P>0.05 vs control).

In rats treated with WBCD+BMP-7 at four weeks 1.7±0.7 (t-test, P>0.01 vs control and P>0.1 vs BMP-1) cortices healed, while at seven weeks 3.2±1.4 (t-test, P>0.01 vs control and P>0.1 vs BMP-1) cortices healed. The callus area was 11.3±3.9 mm$^2$ (t-test, P>0.01 vs control and P>0.1 vs BMP-1), and at seven weeks it was 6.7±2.9 mm$^2$ (t-test, P>0.05 vs control and P>0.1 vs BMP-1).

These results indicate that locally administered BMP-1-1 at an orthotopic site (defect site) in a model of femoral fracture repair significantly accelerated the bone fracture healing as compared to control rats. Surprisingly, when BMP-7 was used in a composition with WBCD, femurs healed faster than in control rats, but were not different from animals treated with BMP-1-1, which is an ECM processing enzyme. BMP-7 is commercially used with bovine collagen as a carrier. Bovine collagen implanted alone in a similar model of bone repair in a rat inhibits bone repair as compared to untreated control rats.

Biomechanical Testing

Three point bending test indicated that BMP-1-1 treated femurs needed a significantly greater maximal load to re-fracture as compared to control femurs treated only with the whole blood-derived coagulum device (no BMP-1-1) (see, Table 2, below). As compared with the femur from the opposite leg (contralateral femur), bones treated with BMP-1-1 required 26% less load to cause re-fracture; whereas control bones needed 51% less load to re-fracture than the normal contralateral bones (see Table 2).

The maximal load needed to break BMP-7 treated bones was not statistically different from those treated with BMP-1-1 (see, Table 2, below). These results confirmed the radiographic findings collectively indicating that BMP-1-1 accelerates bone repair and regeneration of acute fractures in a rat model, and that it is equally as effective as BMP-7 when used with the whole blood-derived coagulum device. Indentation test of trabecular bone indicates that BMP-1-1 treated bones had more trabecular bone than control animals (see, Table 3).

TABLE 2

Results of three point bending test on rat femurs after therapy

| Parameter | Control | BMP-1-1 | BMP-7 | BMP-1 contralateral | BMP-7 contralateral |
|---|---|---|---|---|---|
| Fμ (N) | 119.99 ± 19.77 | 175.32 ± 24.87* | 189.12 ± 28.69* | 212.33 ± 37.82 | 234.56 ± 24.59 |
| S (N/mm) | 266.84 ± 48.81 | 356.12 ± 53.09 | 377.40 ± 39.94 | 390.27 ± 43.30 | 402.75 ± 40.13 |
| W (mJ) | 91.67 ± 23.35 | 106.08 ± 15.54 | 116.06 ± 17.80 | 122.25 ± 18.16 | 131.15 ± 32.65 |
| T (MJ/m$^3$) | 8.65 ± 2.49 | 11.84 ± 1.7 | 11.33 ± 1.5 | 12.12 ± 1.61 | 12.36 ± 3.89 |

*P < 0.01 vs control, one way ANOVA-Dunnett test

TABLE 3

Results of indentation test on rat femurs after therapy

| Parameter | Control | BMP-1-1 | BMP-7 | BMP-1 contralateral | BMP-7 contralateral |
|---|---|---|---|---|---|
| Fμ (N) | 67.47 ± 25.7 | 84.30 ± 13* | 104.95 ± 31* | 101.31 ± 32.73 | 129.13 ± 19.5* |
| S (N/mm) | 93.25 ± 44.33 | 118.03 ± 14.34 | 132.11 ± 32.68* | 180.36 ± 38.6* | 170.54 ± 32.6* |
| W (mJ) | 54.62 ± 14.2 | 83.89 ± 15.1* | 93.65 ± 16.5* | 104.21 ± 25.2* | 106.24 ± 16.8 |
| σ (N/mm$^2$) | 21.49 ± 11.3 | 31.37 ± 1.19 | 43.68 ± 9.8* | 51.61 ± 10.42* | 59.28 ± 6.2* |

*P < 0.01 vs control, one way ANOVA-Dunnett test

Example 13

The release of BMP-4 and BMP-7 into the medium of in vitro cultured rat calvariae explant cultures treated with BMP-1-1 and BMP-1-3.

Rat fetuses that were 18 days old were obtained from pregnant rats and their calvariae were isolated, cleaned, equally sized, and placed into cultures containing bone specific medium as previously described (Vukicevic et al., Proc. Natl. Acad. Sci. USA, 86: 8793 (1989)). Such calvariae explant cultures produce bone cells as well as extracellular matrix (ECM). At 48 hours following culture, the explanted calvariae were treated with 100 ng/ml BMP-1-1 or 100 ng/ml BMP-1-3 daily for a period of 3 days. The medium was collected daily, stored at −20° C., and on day 4 purified over a heparin column. Following purification over a heparin column, the protein concentration was determined and BMP-2, BMP-4, BMP-6, and BMP-7 were detected by immunoblotting as previously described (Simic et al., J. Biol. Chem., 286:13472 (2006)).

The results indicated that in the medium of control cultures there were no detectable amounts of authentic osteogenic BMPs found, while in the medium of calvariae treated with BMP-1-1, the mature domain of BMP-4 was detected, whereas BMP-2, BMP-6 and BMP-7 were not detected. These results indicate that BMP-1-1 has an effect on the release of BMP-4 from culture explants consisting of fetal calvariae rich in bone cells and ECM, which appears to act as a repository of stored authentic BMP molecules (see, also, Martinovic et al., Arch. Cytol. Histol., 1: 23 (2006)). In the medium of cultures treated with BMP-1-3 in addition to BMP-4, BMP-7 was detected, indicating that BMP-1-3 releases more authentic BMPs from ECM than BMP-1-1.

Example 14

Synergistic acceleration of bone defect healing in rabbits treated locally with BMP-1-1 and BMP-7.

Animals

An ulnar segmental-defect model was used to evaluate bone healing in adult male New Zealand White rabbits (3 kg to 4 kg in weight). The implants consisted of blood coagulum as a carrier to which different amounts of recombinant human BMP-1-1 and recombinant human mature BMP-7 were added (Genera Research Laboratory). These animals were compared with animals receiving blood coagulum implant alone (negative control). Rabbits were treated with anti-parasitics one week before surgery. Animals were also given enrofloxacin, by intramuscular injection, at one day before operation and then ten days following surgery.

With the rabbit under anesthesia and analgesia, one forelimb was shaved and then prepared and draped in a sterile fashion. A lateral incision, approximately 2.5 centimeters in length, was made, and the tissues overlying the ulna were dissected. A 1.5-centimeter segmental osteoperiostal defect was created in the middle of the ulna with an oscillating saw. The radius was left intact for mechanical stability, and no internal or external fixation devices were used. After copious irrigation with saline solution to remove bone debris and spilled marrow cells, the implant was packed carefully into place to fill the defect. Coagulum was then overlaid with serum. The soft tissues were closed meticulously in layers to contain the implant. The animals were allowed full weight-bearing activity, water, and rabbit chow.

WBCD Preparation

Blood samples were collected from rabbit marginal ear veins into tubes without any anticoagulants substance in a volume of 1.5 mL, one day before surgery. BMP-1-1 and BMP-7 were added into blood in amounts of 14 μg and 100 μg, respectively. Blood samples were left at 4° C. to coagulate. The next day, samples were centrifuged at 8000×g for 5 minutes. Liquid part (serum) was removed and saved, and coagulum was ready to use.

The rabbits were divided into one of the groups listed below and defects have been treated as follows:

Group 1. Control rabbits treated with the whole blood coagulum device (WBCD) without BMP or BMP-1 isoform only (n=8).

Group 2. Rabbits treated with WBCD containing 14 μg/1.5 mL of BMP-1-1.

Group 3. Rabbits treated with WBCD containing 100 μg/1.5 mL of BMP-7.

Group 4. Rabbits treated with WBCD containing 14 µg/1.5 mL of BMP-1+100 µg of BMP-7/1.5 mL.

Results

The results are shown in FIGS. 5-8. Rabbit ulna defects did not heal in the control rabbits (Group 1) treated with WBCD only (no BMP-1-1, no BMP-7), as observed by X-ray biweekly follow up. The unhealed defect in a representative bone after 6 weeks from the control group is shown in FIGS. 5A and 5B (two views of the same bone).

Figure 6B:
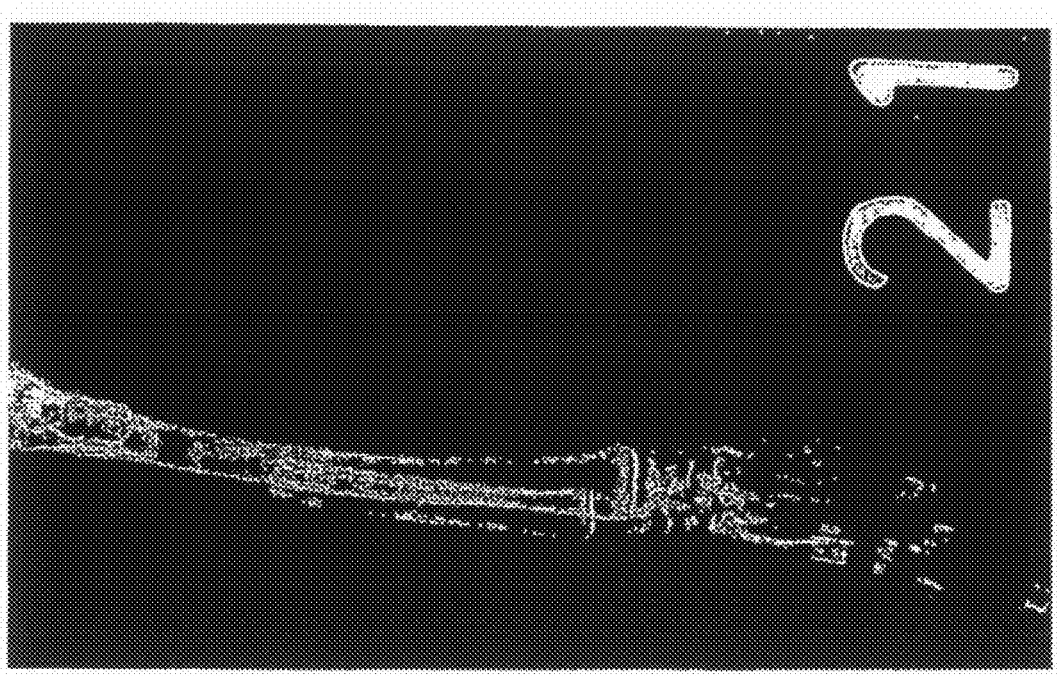
FIGS. 6A and 6B show ulnar defect in representative bone after 6 weeks from rabbits treated locally with a WBCD containing BMP-1-1 as described in Example 14, below.
Figure 6A:
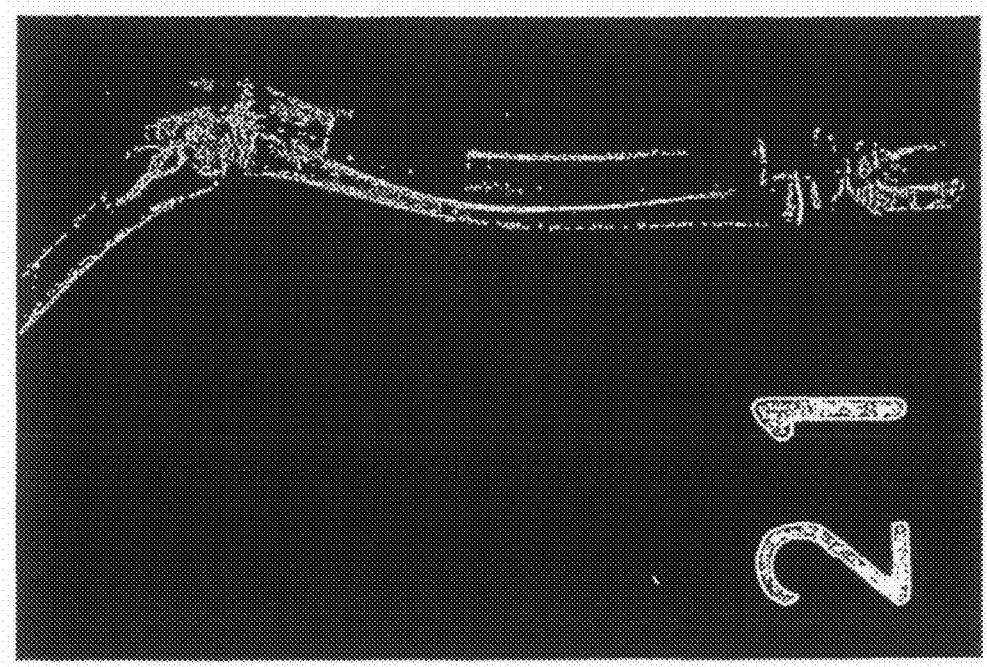

Results after 6 weeks in a representative bone from rabbits treated locally with a WBCD having BMP-1-1 (Group 2) are shown in FIGS. 6A and 6B. Results after 6 weeks in a representative bone from rabbits treated locally with WBCD having BMP-7 (Group 3) are shown in FIGS. 7A and 7B. Results after 6 weeks in a representative bone from rabbits treated locally with WBCD having BMP-1-1 and BMP-7 (Group 3) are shown in FIGS. 8A and 8B. Rabbits treated with BMP-7-containing WBCD (Group 3) rebridged the bone defect at 8 weeks following surgery, while rabbits treated with BMP-1-1-containing WBCD (Group 2) showed initial bone formation as early as two weeks and advanced healing at 8 weeks following surgery. However, rabbits treated locally with a WBCd having a combination of both BMP-1-1 and BMP-7 (Group 4), had a synergistic healing of the ulnar defect with a complete rebridgement of the defect and formation of the new cortex with a pronounced remodelling of newly formed bone as early as 6 weeks (see, FIGS. 8A and 8B).

These results indicate that BMP-1-1 and BMP-7 applied locally at an orthotopic site of a fracture act synergistically to accelerate bone regeneration.

All patents, applications, and publications cited in the above text are incorporated herein by reference.

Other variations and embodiments of the invention described herein will now be apparent to those of skill in the art without departing from the disclosure of the invention or the claims below.

The invention claimed is:

1. A method of treating chronic renal failure in an individual comprising administering systemically to the individual an antibody molecule to a BMP-1-1 isoform, an antibody molecule to a BMP-1-3 isoform, or a combination of the two antibody molecules.

2. The method according to claim 1, wherein an antibody molecule to a BMP-1-3 isoform is administered to the individual.

* * * * *